(12) United States Patent
Von Hoff et al.

(10) Patent No.: US 8,700,335 B2
(45) Date of Patent: Apr. 15, 2014

(54) SYSTEM AND METHOD FOR DETERMINING INDIVIDUALIZED MEDICAL INTERVENTION FOR A DISEASE STATE

(75) Inventors: Daniel D. Von Hoff, Scottsdale, AZ (US); Robert Penny, Lebanon, IN (US)

(73) Assignee: Caris MPI, Inc., Phoenix, AZ (US)

( * ) Notice: Subject to any disclaimer, the term of this patent is extended or adjusted under 35 U.S.C. 154(b) by 1310 days.

(21) Appl. No.: 11/750,721

(22) Filed: May 18, 2007

(65) Prior Publication Data

US 2008/0014146 A1 Jan. 17, 2008

Related U.S. Application Data

(60) Provisional application No. 60/747,645, filed on May 18, 2006.

(51) Int. Cl.
*G01N 33/48* (2006.01)

(52) U.S. Cl.
USPC .......................................................... 702/19

(58) Field of Classification Search
USPC .......................................................... 702/19
See application file for complete search history.

(56) References Cited

U.S. PATENT DOCUMENTS

| | | | |
|---|---|---|---|
| 4,725,550 A | 2/1988 | Perucho et al. |
| 4,877,867 A | 10/1989 | Shalitin |
| 4,957,859 A | 9/1990 | Bizub et al. |
| 5,496,699 A | 3/1996 | Sorenson |
| 5,610,281 A | 3/1997 | Brenner et al. |
| 5,693,473 A | 12/1997 | Shattuck-Eidens et al. |
| 5,710,001 A | 1/1998 | Skolnick et al. |
| 5,747,282 A | 5/1998 | Skolnick et al. |
| 5,753,441 A | 5/1998 | Skolnick et al. |
| 5,837,492 A | 11/1998 | Tavtigian et al. |
| 5,895,748 A | 4/1999 | Johnson et al. |
| 5,997,866 A | 12/1999 | Johnson et al. |
| 5,998,151 A | 12/1999 | Johnston et al. |
| 6,013,431 A | 1/2000 | Soderlund et al. |
| 6,033,857 A | 3/2000 | Tavtigian et al. |
| 6,090,546 A | 7/2000 | Breivik et al. |
| 6,124,104 A | 9/2000 | Tavtigian et al. |
| 6,150,514 A | 11/2000 | Swensen |
| 6,218,122 B1 | 4/2001 | Friend et al. |
| 6,221,620 B1 | 4/2001 | Johnston et al. |
| 6,262,242 B1 | 7/2001 | Steck et al. |
| 6,300,080 B1 | 10/2001 | Brenner et al. |
| 6,406,870 B2 | 6/2002 | Brenner et al. |
| 6,416,987 B1 | 7/2002 | Liu-Chen et al. |
| 6,482,795 B1 | 11/2002 | Steck et al. |
| 6,586,177 B1 | 7/2003 | Shuber |
| 6,649,359 B2 | 11/2003 | Mutter et al. |
| 6,812,023 B1 | 11/2004 | Lamparski et al. |
| 7,029,676 B2 | 4/2006 | Brenner et al. |
| 7,049,059 B2 | 5/2006 | Danenberg |
| 7,081,340 B2 | 7/2006 | Baker et al. |
| 7,129,040 B2 | 10/2006 | Steck et al. |
| 7,154,219 B2 | 12/2006 | Hamada et al. |
| 7,163,789 B2 | 1/2007 | Chen et al. |
| 7,217,795 B2 | 5/2007 | Steck et al. |
| 7,250,497 B2 | 7/2007 | Scholl et al. |
| 7,319,007 B2 | 1/2008 | Cybulski et al. |
| 7,442,507 B2 | 10/2008 | Polsky et al. |
| 7,526,387 B2 | 4/2009 | Baker et al. |
| 7,560,226 B2 | 7/2009 | Christopherson et al. |
| 7,593,913 B2 | 9/2009 | Wang et al. |
| 2001/0018189 A1 | 8/2001 | Brenner et al. |
| 2002/0095260 A1 | 7/2002 | Huyn |
| 2002/0150966 A1 | 10/2002 | Muraca |
| 2002/0192724 A1 | 12/2002 | Brenner et al. |
| 2003/0091994 A1 | 5/2003 | Jenkins et al. |
| 2003/0219767 A1 | 11/2003 | Ayers et al. |
| 2004/0058352 A1 | 3/2004 | Stein et al. |
| 2004/0152112 A1 | 8/2004 | Croce |
| 2004/0191817 A1 | 9/2004 | Scott et al. |
| 2004/0265813 A1 | 12/2004 | Takechi et al. |
| 2005/0084913 A1 | 4/2005 | Punnonen et al. |
| 2005/0186584 A1 | 8/2005 | Stratton et al. |
| 2005/0221398 A1 | 10/2005 | Jacquemier et al. |
| 2005/0244880 A1 | 11/2005 | Kallioniemi et al. |
| 2005/0260646 A1 | 11/2005 | Baker et al. |
| 2005/0287543 A1 | 12/2005 | Yu et al. |
| 2006/0019256 A1 | 1/2006 | Clarke et al. |
| 2006/0134664 A1 | 6/2006 | Scherzer et al. |

(Continued)

FOREIGN PATENT DOCUMENTS

| | | | |
|---|---|---|---|
| EP | 1260520 A2 | 11/2002 |
| EP | 1260520 A3 | 12/2002 |

(Continued)

OTHER PUBLICATIONS

Holzbeierlein (An J Path, 2004, vol. 164, pp. 217-227).*
Ciardiello et al. (Clin Cancer Res, 2001, vol. 7, pp. 2958-2970).*
Di Lorenzo (Clin Cancer Res, 2002, vol. 8, pp. 3438-3444).*
Madaan (BJU Int. 2000 vol. 86, pp. 736-741).*
Latil (Cancer Res 2001 vol. 61, pp. 191-1926).*
Paronetto (AJP, 2004, vol. 164, pp. 1243-1251).*
Awada (Critical Reviews in Oncology/Hemoatology, 2003, vol. 48, pp. 43-63).*
Ross (Am J Clin Pathol, 2004, vol. 122, pp. 598-609).*
Brown, et al. Activation of SPARC Expression in Reactive Stroma Associated with Human Epithelial Ovarian Cancer. Gynecologic oncology. 1999;75(1):25-33.
Infante, et al. Peritumoral fibroblast SPARC expression and patient outcome with resectable pancreatic adenocarcinoma. J Clin Oncol. Jan. 20, 2007;25(3):319-25.

(Continued)

*Primary Examiner* — Jerry Lin
(74) *Attorney, Agent, or Firm* — Ramin Akhavan

(57) ABSTRACT

A system and method for determining individualized medical intervention for a particular disease state, and especially for cancers, that includes the molecular profiling of a biological sample from the patient, determining whether any molecular findings including one or more genes, one or more gene expressed proteins, one or more molecular mechanisms, and/or combinations of such exhibit a change in expression compared to a reference, and identifying a non-specific disease therapy or agent capable of interacting with the genes, gene expressed proteins, molecular mechanisms, or combinations of such molecular findings that exhibited a change in expression.

17 Claims, 28 Drawing Sheets

(56) References Cited

U.S. PATENT DOCUMENTS

| | | |
|---|---|---|
| 2006/0147959 A1 | 7/2006 | Bell et al. |
| 2006/0275844 A1 | 12/2006 | Linke et al. |
| 2007/0009966 A1 | 1/2007 | Pommer et al. |
| 2007/0020657 A1 | 1/2007 | Grebe et al. |
| 2007/0050146 A1 | 3/2007 | Bentwich et al. |
| 2007/0054333 A1 | 3/2007 | Steck et al. |
| 2007/0059758 A1 | 3/2007 | Levine |
| 2007/0065845 A1 | 3/2007 | Baker et al. |
| 2007/0071762 A1 | 3/2007 | Ts'o et al. |
| 2007/0099209 A1 | 5/2007 | Clarke et al. |
| 2007/0105105 A1 | 5/2007 | Clelland et al. |
| 2007/0117133 A1 | 5/2007 | Trieu et al. |
| 2007/0134687 A1 | 6/2007 | Georges et al. |
| 2007/0141589 A1 | 6/2007 | Baker et al. |
| 2007/0172844 A1 | 7/2007 | Lancaster et al. |
| 2007/0172857 A1 | 7/2007 | Diato et al. |
| 2007/0178445 A1 | 8/2007 | Eshleman et al. |
| 2007/0207489 A1 | 9/2007 | Pestano et al. |
| 2007/0224208 A1 | 9/2007 | Guo et al. |
| 2007/0243552 A1 | 10/2007 | Williams et al. |
| 2007/0254295 A1 | 11/2007 | Harvey et al. |
| 2007/0292412 A1 | 12/2007 | Salonen et al. |
| 2008/0004233 A1 | 1/2008 | Malafa et al. |
| 2008/0009005 A1 | 1/2008 | Kruk |
| 2008/0014146 A1 | 1/2008 | Von Hoff et al. |
| 2008/0014598 A1 | 1/2008 | Wiederhold et al. |
| 2008/0038271 A1 | 2/2008 | Amler et al. |
| 2008/0050387 A1 | 2/2008 | Chang |
| 2008/0064049 A1 | 3/2008 | Clarke et al. |
| 2008/0090233 A1 | 4/2008 | Garcia et al. |
| 2008/0096768 A1 | 4/2008 | Laird et al. |
| 2008/0160517 A1 | 7/2008 | Danenberg |
| 2008/0213280 A1 | 9/2008 | Benyunes |
| 2008/0220418 A1 | 9/2008 | Ballhause et al. |
| 2008/0226645 A1 | 9/2008 | O'toole et al. |
| 2008/0242622 A1 | 10/2008 | Lowe et al. |
| 2008/0268449 A1 | 10/2008 | Hoon |
| 2008/0293055 A1 | 11/2008 | Freeman et al. |
| 2008/0312199 A1 | 12/2008 | Glinsky |
| 2008/0318223 A1 | 12/2008 | Scholl et al. |
| 2008/0318224 A1 | 12/2008 | Scholl et al. |
| 2008/0318230 A1 | 12/2008 | Agus et al. |
| 2009/0017012 A1 | 1/2009 | Bepler |
| 2009/0061422 A1 | 3/2009 | Linke et al. |
| 2009/0061454 A1 | 3/2009 | Brody et al. |
| 2009/0075267 A1 | 3/2009 | Siena et al. |
| 2009/0092983 A1 | 4/2009 | Birnbaum et al. |
| 2009/0098538 A1 | 4/2009 | Glinsky |
| 2009/0098553 A1 | 4/2009 | Guilford |
| 2009/0098554 A1 | 4/2009 | Ge |
| 2009/0118175 A1 | 5/2009 | Macina |
| 2009/0130125 A1 | 5/2009 | Loibner et al. |
| 2009/0155798 A1 | 6/2009 | Ring et al. |
| 2009/0170715 A1 | 7/2009 | Glinsky |
| 2009/0181406 A1 | 7/2009 | Ridder et al. |
| 2009/0197255 A1 | 8/2009 | Cybulski et al. |
| 2009/0203015 A1 | 8/2009 | Chang et al. |
| 2009/0215642 A1 | 8/2009 | Knudson et al. |
| 2009/0226902 A1 | 9/2009 | Drexhage et al. |
| 2009/0233279 A1 | 9/2009 | Glinskii |
| 2009/0258436 A1 | 10/2009 | Hornbeck et al. |
| 2009/0280490 A1 | 11/2009 | Baker et al. |
| 2009/0280493 A1 | 11/2009 | Wirtz et al. |
| 2009/0311702 A1 | 12/2009 | Shak et al. |
| 2010/0055724 A1 | 3/2010 | Taylor et al. |
| 2010/0069298 A1 | 3/2010 | Penny et al. |
| 2010/0092524 A1 | 4/2010 | Taylor et al. |
| 2010/0113299 A1 | 5/2010 | Von Hoff et al. |
| 2011/0230360 A1 | 9/2011 | Stephan et al. |

FOREIGN PATENT DOCUMENTS

| | | |
|---|---|---|
| EP | 1394272 B1 | 3/2006 |
| EP | 0785216 B2 | 6/2006 |
| EP | 1892303 A1 | 2/2008 |
| EP | 1947194 A1 | 7/2008 |
| EP | 0705902 B2 | 8/2008 |
| EP | 1668152 B1 | 8/2008 |
| EP | 1983002 A2 | 10/2008 |
| EP | 2000543 A2 | 12/2008 |
| EP | 1983002 A3 | 3/2009 |
| EP | 2036990 A1 | 3/2009 |
| EP | 1244047 | 4/2009 |
| EP | 0705903 B2 | 8/2009 |
| EP | 2105511 A1 | 9/2009 |
| EP | 0699754 B2 | 12/2009 |
| EP | 1642968 | 11/2011 |
| GB | 2327497 A | 1/1999 |
| WO | WO 95/29693 A1 | 11/1995 |
| WO | WO 98/33907 A1 | 8/1998 |
| WO | WO 01/18627 A1 | 3/2001 |
| WO | WO 02/16429 | 2/2002 |
| WO | WO 02/16581 | 2/2002 |
| WO | WO 02/16602 | 2/2002 |
| WO | WO 02/65118 A1 | 2/2002 |
| WO | WO 03/006973 A1 | 1/2003 |
| WO | WO 03/078662 A1 | 9/2003 |
| WO | WO 2004/060270 | 7/2004 |
| WO | WO 2004/060270 A1 | 7/2004 |
| WO | WO 2005/039382 A2 | 5/2005 |
| WO | WO 2005/054512 A2 | 6/2005 |
| WO | WO 2005/067391 A2 | 7/2005 |
| WO | WO 2005/100606 A2 | 10/2005 |
| WO | WO 2005/054512 A3 | 11/2005 |
| WO | WO 2005/118875 A2 | 12/2005 |
| WO | WO 2005/121369 A2 | 12/2005 |
| WO | WO 2005/039382 A3 | 1/2006 |
| WO | WO 2006/004910 A2 | 1/2006 |
| WO | WO 2005/121369 A3 | 5/2006 |
| WO | WO 2006/054991 A1 | 5/2006 |
| WO | WO 2005/100606 A3 | 6/2006 |
| WO | WO 2006/004910 A2 | 6/2006 |
| WO | WO 2006/087233 A2 | 8/2006 |
| WO | WO 2006/087233 A3 | 11/2006 |
| WO | WO 2007/001868 A1 | 1/2007 |
| WO | WO 2005/067391 A3 | 10/2007 |
| WO | WO 2007/114896 A2 | 10/2007 |
| WO | WO 2007/114896 A3 | 1/2008 |
| WO | WO 2008/008284 A2 | 1/2008 |
| WO | WO 2008/063414 A2 | 1/2008 |
| WO | WO 2008/021483 A2 | 2/2008 |
| WO | WO 2008/028926 A2 | 3/2008 |
| WO | WO 2008/057305 A2 | 5/2008 |
| WO | WO 2008/063413 A2 | 5/2008 |
| WO | WO 2008/069881 A2 | 6/2008 |
| WO | WO 2008/076447 A2 | 6/2008 |
| WO | WO 2008/028926 A3 | 7/2008 |
| WO | WO 2008/079269 A2 | 7/2008 |
| WO | WO 2008/082730 A2 | 7/2008 |
| WO | WO 2008/099280 A2 | 8/2008 |
| WO | WO 2008/063413 A3 | 9/2008 |
| WO | WO 2008/108986 A2 | 9/2008 |
| WO | WO 2008/112283 A2 | 9/2008 |
| WO | WO 2008/115419 A2 | 9/2008 |
| WO | WO 2008/099280 A3 | 10/2008 |
| WO | WO 2008/121132 A2 | 10/2008 |
| WO | WO 2008/123866 A2 | 10/2008 |
| WO | WO 2008/123867 A1 | 10/2008 |
| WO | WO 2008/008284 A3 | 11/2008 |
| WO | WO 2008/138578 A2 | 11/2008 |
| WO | WO 2008/143639 A2 | 11/2008 |
| WO | WO 2008/057305 A3 | 12/2008 |
| WO | WO 2008/079269 A3 | 12/2008 |
| WO | WO 2008/123866 A3 | 12/2008 |
| WO | WO 2008/151004 A1 | 12/2008 |
| WO | WO 2008/063414 A3 | 1/2009 |
| WO | WO 2008/069881 A3 | 1/2009 |
| WO | WO 2008/076447 A3 | 1/2009 |
| WO | WO 2008/082730 A3 | 1/2009 |
| WO | WO 2008/108986 A3 | 2/2009 |
| WO | WO 2008/123867 A9 | 2/2009 |
| WO | WO 2008/151004 A9 | 2/2009 |
| WO | WO 2009/021322 A1 | 2/2009 |

(56) References Cited

FOREIGN PATENT DOCUMENTS

| | | |
|---|---|---|
| WO | WO 2008/021483 A3 | 3/2009 |
| WO | WO 2008/112283 A3 | 3/2009 |
| WO | WO 2008/115419 A3 | 3/2009 |
| WO | WO 2008/121132 A3 | 3/2009 |
| WO | WO 2008/138578 A3 | 3/2009 |
| WO | WO 2009/036236 A1 | 3/2009 |
| WO | WO 2006/004910 A3 | 4/2009 |
| WO | WO 2009/052573 A1 | 4/2009 |
| WO | WO 2008/143639 A3 | 5/2009 |
| WO | WO 2009/061297 A1 | 5/2009 |
| WO | WO 2005/118875 A3 | 6/2009 |
| WO | WO 2009/103542 A1 | 8/2009 |
| WO | WO 2009/103790 A2 | 8/2009 |
| WO | WO 2009/108860 A2 | 9/2009 |
| WO | WO 2009/118204 A2 | 10/2009 |
| WO | WO 2009/124251 A1 | 10/2009 |
| WO | WO 2009/126160 A1 | 10/2009 |
| WO | WO 2009/103790 A3 | 11/2009 |
| WO | WO 2009/118204 A3 | 11/2009 |
| WO | WO 2009/134944 A2 | 11/2009 |
| WO | WO 2009/002931 A2 | 12/2009 |
| WO | WO 2009/108860 A3 | 1/2010 |
| WO | WO 2009/134944 A3 | 2/2010 |
| WO | WO 2010/028288 A2 | 3/2010 |

OTHER PUBLICATIONS

International search report dated Jan. 14, 2008 for PCT Application No. US2007/69286.

International search report dated Apr. 30, 2010 for PCT Application No. US2009/57161.

Rugo, H. S. New treatments for metastatic breast cancer: mechanisms of action of nanoparticle albumin-bound taxanes. Commun Oncol 2008;5(suppl 4):8-12.

Simpson, et al. Exosomes: proteomic insights and diagnostic potential. Expert Rev Proteomics. Jun. 2009;6(3):267-83.

Thery, et al. Membrane vesicles as conveyors of immune responses. Nat Rev Immunol. Aug. 2009;9(8):581-93. Epub Jun. 5, 2009.

Thomas, et al. Differential expression of osteonectin/SPARC during human prostate cancer progression. Clin Cancer Res. Mar. 2000;6(3):1140-9.

Tong, et al. MicroRNA profile analysis of human prostate cancers. Cancer Gene Ther. Mar. 2009;16(3):206-16.

Watkins, et al. Increased levels of SPARC (osteonectin) in human breast cancer tissues and its association with clinical outcomes. Prostaglandins Leukot Essent Fatty Acids. Apr. 2005;72(4):267-72.

Altieri, D.C. Survivin, cancer networks and pathway-directed drug discovery. Nat Rev Cancer. Jan. 2008;8(1):61-70.

Andre, et al. Malignant effusions and immunogenic tumour-derived exosomes. Lancet. Jul. 27, 2002;360(9329):295-305.

Bard, et al. Proteomic analysis of exosomes isolated from human malignant pleural effusions. Am J Respir Cell Mol Biol. Jul. 2004;31(1):114-21. Epub Feb. 19, 2004.

Bartel. MicroRNAs: Genomics, biogenesis, mechanism, and function. Cell. Jan. 23, 2004;116(2):281-97.

Berek, et al. Biologic and immunologic therapies for ovarian cancer. J Clin Oncol. May 15, 2003;21(10 Suppl):168s-174s.

Bjorge, et al. Identification of protein-tyrosine phosphatase 1B as the major tyrosine phosphatase activity capable of dephosphorylating and activating c-Src in several human breast cancer cell lines. J Biol Chem. Dec. 29, 2000;275(52):41439-46.

Blower, et al. MicroRNAs modulate the chemosensitivity of tumor cells. Mol Cancer Ther. Jan. 2008;7(1):1-9.

Calin, et al. MicroRNA signatures in human cancers. Nature Rev Cancer. Nov. 2006;6(11):857-66.

Calin, et al. MicroRNA-cancer connection: the beginning of a new tale. Cancer Res. Aug. 1, 2006;66(15):7390-4.

Choi, et al. Proteomic Analysis of Microvesicles Derived from Human Colorectal Cancer Cells. Journal of Proteome Research. 2007;6(12):4646-4655.

Christiansen, et al. Mutations of Genes in the Receptor Tyrosine Kinase (RTK)/RASBRAF Signal Transduction Pathway in Therapy-Related Myelodysplasia and Acute Myeloid Leukemia. Leukemia. 2005;19(12):2232-40.

Cummins, et al. Implications of micro-RNA profiling for cancer diagnosis. Oncogene. Oct. 9, 2006;25(46):6220-7. Review.

De Cecco, et al. Gene expression profiling of advanced ovarian cancer: Characteristization of a molecular signature involving fibroblast growth factor 2. Oncogene. Oct. 21, 2004;23(49):8171-83.

Escola, et al. Selective enrichment of tetraspan proteins on the internal vesicles of multivesicular endosomes and on exosomes secreted by human B-lymphocytes. J Biol Chem. Aug. 7, 1998;273(32):20121-7.

Esquela-Kerscher, et al. Oncomirs—microRNAs with a role in cancer. Nature Rev Cancer. Apr. 2006;6(4):259-69.

Gaur, et al. Characterization of microRNA expression levels and their biological correlates in human cancer cell lines. Cancer Res. Mar. 15, 2007;67(6):2456-68.

Hoorn, et al. Prospects for urinary proteomics: exosomes as a source of urinary biomarkers. Nephrology (Carlton). Jun. 2005;10(3):283-90.

International search report dated Jun. 16, 2010 for PCT Application No. US2009/060630.

International search report dated Jul. 20, 2010 for PCT Application No. US10/00407.

International search report dated Jul. 21, 2010 for PCT Application No. US2009/006095.

Iorio, et al. MicroRNA gene expression deregulation in human breast cancer. Cancer Res. Aug. 15, 2005;65(16):7065-70.

Iorio, et al. MicroRNA signatures in human ovarian cancer. Cancer Res. Sep. 15, 2007;67(18):8699-707.

Koga, et al. Purification, characterization and biological significance of tumor-derived exosomes. Anticancer Res. Nov.-Dec. 2005;25(6A):3703-7.

Lu, et al. MicroRNA expression profiles classify human cancers. Nature. 2005; 435:834-838.

Mears, et al. Proteomic analysis of melanoma-derived exosomes by two-dimensional polyacrylamide gel electrophoresis and mass spectrometry. Proteomics. Dec. 2004;4(12):4019-31.

Menon, et al. Recent developments in ovarian cancer screening. Curr Opin Obstet Gynecol. Feb. 2000;12(1):39-42.

Miska. How microRNAs control cell division, differentiation, and death. Curr Opin Genet Dev. Oct. 2005;15(5):563-8.

Olver, et al. Proteomic analysis of secreted exosomes. Subcell Biochem. 2007;43:99-131.

Pisitkun, et al. Identification and proteomic profiling of exosomes in human urine. PNAS. 2004; 101(36):13368-13373.

Raposo, et al. Accumulation of major histocompatibility complex class II molecules in mast cell secretory granules and their release upon degranulation. Mol Biol Cell. Dec. 1997;8(12):2631-45.

Ratajczak, et al. Embryonic stem cell-derived microvesicles reprogram hematopoietic progenitors: Evidence for horizontal transfer of mRNA and protein delivery. Leukemia. May 2006;20(5):847-56.

Ratajczak, et al. Membrane-derived microvesicles: important and underappreciated mediators of cell-to-cell communication. Leukemia. Sep. 2006;20(9):1487-95.

Rodrigues, et al. 99mTc-depreotide scintigraphy versus 18F-FDG-PET in the diagnosis of radioiodine-negative thyroid cancer. J Clin Endocrinol Metab. Oct. 2006;91(10):3997-4000.

Ruiz, et al. Integration of Gene Dosage and Gene Expression in Non-Small Cell Lung Cancer, Identification of HSP90 as Potential Target. PLoS One. 2008;3(3)e1722:1-7.

Runz, et al. Malignant ascites-derived exosomes of ovarian carcinoma patients contain CD24 and EpCAM. Gynecol Oncol. Dec. 2007;107(3):563-71.

Sabapatha, et al. Specific isolation of placenta-derived exosomes from the circulation of pregnant women and their immunoregulatory consequences. Am J Reprod Immunol. Nov.-Dec. 2006;56(5-6):345-55.

Sankaranarayanan, et al. Worldwide burden of gynaecological cancer: the size of the problem. Best Pract Res Clin Obstet Gynaecol. Apr. 2006;20(2):207-25.

(56) References Cited

OTHER PUBLICATIONS

Seligson, et al. Epithelial cell adhesion molecule (KSA) expression: pathobiology and its role as an independent predictor of survival in renal cell carcinoma. Clin Cancer Res. Apr. 15, 2004;10(8):2659-69.
She, et al. Breast Tumor Cells with P13K Mutation or HER2 Amplification Are Selectively Addicted to Akt Signaling. PLoS One. 2008;3(8)e3065:1-10.
Shishodia, et al. N-(4-Hydroxyphenyl)Retinamide Inhibits Invasion, Suppresses Osteoclastogenesis, and Potentiates Apoptosis through Down-regulation of IKBA Kinase and Nuclear Factor-KB-Regulated Gene Products. Cancer Research. 2005;65(20):9555-65.
Simpson, et al. Proteomic profiling of exosomes: current perspectives. Proteomics. Oct. 2008;8(19):4083-99.
Taylor, et al. Binding of specific peroxidase-labeled antibody to placental-type phosphatase on tumor-derived membrane fragments. Cancer Res. Nov. 1980;40(11):4064-9.
Taylor, et al. Isolation of plasma membrane fragments from cultured murine melanoma cells. Biochem Biophys Res Commun. Jun. 15, 1983;113(2):470-6.
Taylor, et al. MicroRNA signatures of tumor-derived exosomes as diagnostic biomarkers of ovarian cancer. Gynecol Oncol. Jul. 2008;110(1):13-21.
Taylor, et al. Pregnancy-associated exosomes and their modulation of T cell signaling. J Immunol Feb. 1, 2006;176(3):1534-42.
Taylor, et al. Pregnancy-linked suppression of TcR signaling pathways by a circulating factor absent in recurrent spontaneous pregnancy loss (RPL). Mol Immunol Apr. 2006;43(11):1872-80.
Taylor, et al. Shed membrane fragment-associated markers for endometrial and ovarian cancers. Gynecol Oncol. Mar. 2002;84(3):443-8.
Taylor, et al. Shedding of plasma membrane fragments. Neoplastic and developmental importance. Dev Biol (NY 1985). 1986;3:33-57.
Taylor, et al. Tumour-derived exosomes and their role in cancer-associated T-cell signalling defects. Br J Cancer. Jan. 31, 2005;92(2):305-11.
Valadi, et al. Exosome-mediated transfer of mRNAs and microRNAs is a novel mechanism of genetic exchange between cells. Nature Cell Biology. 2007; 9(6):654-659.
Valenti, et al. Human tumor-released microvesicles promote the differentiation of myeloid cells with transforming growth factor-beta-mediated suppressive activity on T lymphocytes. Cancer Res 2006; 66: 9290-8.
Yang, et al. MicroRNA expression profiling in human ovarian cancer: miR-214 induces cell survival and cisplatin resistance by targeting PTEN. Cancer Res. Jan. 15, 2008;68(2):425-33.
Yu, et al. The regulation of exosome secretion: a novel function of the p53 protein. Cancer Res. May 1, 2006;66(9):4795-801.
Zhang, et al. microRNAs as oncogenes and tumor suppressors. Dev Biol. Feb. 1, 2007;302(1):1-12.
Zhang, et al. microRNAs exhibit high frequency genomic alterations in human cancer. Proc Natl Acad Sci U S A. Jun. 13, 2006;103(24):9136-41.
Agulnik, et al. Predictive and pharmacodynamic biomarker studies in tumor and skin tissue samples of patients with recurrent or metastatic squamous cell carcinoma of the head and neck treated with erlotinib. J Clin Oncol. Jun. 1, 2007;25(16):2184-90.
Amado, et al. Wild-Type KRAS Is Required for Panitumumab Efficacy in Patients With Metastatic Colorectal Cancer. J Clin Oncol. Apr. 1, 2008;26(10):1626-34.
Arriola, et al. Topoisomerase II alpha amplification may predict benefit from adjuvant anthracyclines in HER2 positive early breast cancer. Br Cancer Res Treat 2007;106:181-189.
Azuma, et al. Excision repair cross-complementation group 1 predicts progression-free and overall survival in non-small cell lung cancer patients treated with platinum-based chemotherapy. Cancer Sci. Sep. 2007;98(9):1336-43.
Barbareschi, et al. Different prognostic roles of mutations in the helical and kinase domains of the PIK3CA gene in breast carcinomas. Clin Cancer Res. Oct. 2007;13(20):6064-9.

Bepler, et al. RRM1 modulated in vitro and in vivo efficacy of gemcitabine and platinum in non-small-cell lung cancer. J Clin Oncol. 2006;24(29):4731-7.
Berns, et al. A functional genetic approach identifies the PI3K pathway as a major determinant of trastuzumab resistance in breast cancer. Cancer Cell. 2007;12(4):395-402.
Birhiray, et al. Phenotypic transformation of CD52(pos) to CD52(neg) leukemic T cells as a mechanism for resistance to CAMPATH-1H. Leukemia. 2002;16(5):861-4.
Blanke, et al. Long-term results from a randomized phase II trial of standard-versus higher-dose imatinib mesylate for patients with unresectable or metastatic gastrointestinal stromal tumors expressing KIT. J Clin Oncol. 2008;26(4):620-625.
Blanke, et al. Phase III randomized, intergroup trial assessing imatinib mesylate at two dose levels in patients with unresectable or metastatic gastrointestinal stromal tumors expressing the kit receptor tyrosine kinase: S0033. J Clin Oncol. Feb. 1, 2008;26(4):626-32.
Boukovinas, et al. Tumor BRCA1, RRM1 and RRM2 mRNA Expression Levels and Clinical Response to First-Line Gemcitabine plus Docetaxel in Non-Small-Cell Lung Cancer Patients. Plos One. Nov. 2008;3(11):1-8.
Brase, et al. ERBB2 and TOP2A in Breast Cancer: A comprehensive analysis of gene amplification, RNA levels, and protein expression and their influence on prognosis and prediction. Clin Cancer Res. 2010;16(8):2391-2401.
Braun, et al. Predictive biomarkers of chemotherapy efficacy in colorectal cancer: results from the UK MRC Focus trial. J Clin Oncol. 2008;26(16):2690-8.
Buckingham, et al. The prognostic value of chr 7 polysomy in NSCLC pts treated with gefitinib. J Thorac Oncol. 2007;2:414-422.
Burger, et al. RNA Expression of Breast Cancer Resistance Protein, Lung Resistance-related Protein, Multidrug Resistance-associated Proteins 1 and 2, and Multidrug Resistance Gene 1 in Breast Cancer, Clinical Cancer Research. Feb. 2003;9:827-836.
Cappuzzo, et al. Primary resistance to cetuximab therapy in EGFR Fish-positive colorectal cancer patients. Br J Cancer. 2008;99(1):83-9.
Cappuzzo, et al. Epidermal growth factor receptor gene and protein and gefitinib sensitivity in non-small-cell lung cancer, J Natl Cancer Inst. 2005;97(9):643-55.
Ceppi, et al. ERCC1 and RRM1 gene expressions but not EGFR are predictive of shorter survival in advanced non-small-cell lung cancer treated with cisplatin and gemcitabine. Annals of Oncology. Sep. 2006;17:1818-1825.
Chan, et al. Aspirin use and survival after diagnosis of colorectal cancer. JAMA. 2009;302(6):649-658.
Cheang, et al. Ki67 index, HER2 status, and prognosis of patients with luminal B breast cancer. J Natl Cancer Inst. 2009;101(10):736-50.
Chinot, et al. Correlation between O6-methylguanine-DNA methyltransferase and survival in inoperable newly diagnosed glioblastoma patients treated with neoadjuvant temozolomide. J Clin Oncol. 2007;25(12):1470-5.
Chintamani, et al. Role of p-glycoprotein expression in predicting response to neoadjuvant chemotherapy in breast cancer—a prospective clinical study. World J Surg Oncol. 2005;3(61):1-9.
Christianson, et al. NH2-terminally truncated her-2 neu protein—and prognosis in breast cancer. Cancer Research. 1998;58:5123-5129.
Dahabreh, et al. Somatic EGFR mutation and gene copy gain as predictive biomarkers for response to tyrosine kinase inhibitors in non small cell lung cancer. Clin Can Res. 2010;16(1):291-303.
De Azambuja, et al. KI-67 as a prognostic marker in early breast cancer. Br JL of Cancer. 2007;96:1504-1513.
De Pas, et al. Brief report. Activity of imatinib in a pt with PDGFR positive malignant solitary fibrous tumor of the pleura. JL of Thoracic Oncology. 2008;3(8):938-941.
De Roock, et al. Effects of KRAS, BRAF, NRAS, and PIK3CA mutations on the efficacy of cetuximab plus chemotherapy in chemotherapy-refractory metastatic colorectal cancer: a retrospective consortium analysis. The Lancet. 2010;11(8):753-762.
De Roock, et al., "KRAS wild-type state predicts survival and is associated to early radiological response in metastatic colorectal cancer treated with cetuximab." Ann Oncol. 2008;19(3):508-15.

(56) References Cited

OTHER PUBLICATIONS

Di Fiore, et al. Clinical relevance of KRAS mutation detection in metastatic colorectal cancer treated by Cetuximab plus chemotherapy. Br JL Cancer. 2007;96:1166-1169.
Di Nicolantonio, et al., Wild-type BRAF is required for response to panitumumab or cetuximab in metastatic colorectal cancer. J Clin Oncol. 2008;26(35):5705-12.
Dil Leo, et al. p.53 Gene mutations as a predictive marker in a population of advanced BC pts randomly treated with dox or docetaxel. Annals of Oncology. 2007;18:997-1003.
Dingemans, et al. Expression of DNA Topoisomerase II-α and Topoisomerase II-β Genes Predicts Survival and Response to Chemotherapy in Patients with Small Cell Lung Cancer. Clin Cancer Res. 1999;(5):2048-2058.
Dowsett, et al. Prognostic Value of Ki67 Expression. JL of Nat. Cancer Inst. 2007 http://jnci.oxfordjournals.org/cgi/content/full/99/2/167.
Dowsett, et al. Relationship between quantitative estrogen and progesterone receptor expression and human epidermal growth factor receptor 2 (HER-2) status with recurrence in the Arimidex, Tamoxifen, Alone or in Combination trial. J Clin Oncol 2008;26(7):1059-65.
Durbecq, et al. Topoisomerase-II alpha expression as a predictive marker in a population of advanced breast cancer patients randomly treated either with single-agent doxorubicin or single-agent docetaxel. Mol Cancer Ther. 2004;3(10):1207-14.
Eberhard, et al. Mutations in epiderinal growth factor receptor and in KRAS are predictive and prognostic indicators in patients with non-small-cell lung cancer treated with chemotherapy alone and in combination with erlotinib. J Clin Oncol. 2005;23(25):5900-9.
El Sheikh, et al. Predictive value of PTEN and AR coexpression of sustained responsiveness to hormonal therapy in prostate cancer—a pilot study. Neoplasia. 2008;10(9):949-53.
Elledge, et al. Estrogen receptor (ER) and progesterone receptor (PgR), by ligand-binding assay compared with ER, PgR and pS2, by immuno-histochemistry in predicting response to tamoxifen in metastatic breast cancer: a Southwest Oncology Group Study. Int J Cancer. 2000;89(2): 111-7.
Endoh, et al. PTEN and PIK3CA expression is associated with prolonged surivival after gefetinib treatment in EGFR mutated LC pts. JL of Thor Oncology. 2006;1(7):629-634.
Filipits, et al. Clinical role of multidrug resistance protein 1 expression in chemotherapy resistance in early-stage breast cancer: the Austrian Breast and Colorectal Cancer Study Group. J Clin Oncol. 2005;23(6):1161-8.
Filipits, et al. Multidrug resistance-associated protein in acute myeloid leukemia: No impact on treatment outcome. Clin Cancer Res. 1997;3(8):1419-25.
Frattini, et al. PTEN loss of expression predicts cetuximab efficacy in metastatic colorectal cancer patients. Br J of Cancer. 2007;97:1139-1145.
Fujita, et al. PTEN activity could be a predictive marker of trastuzumab efficacy in the treatment of ErbB2-overexpressing breast cancer. Br J Cancer. 2006;94(2):247-52.
Heinrich, et al. Primary and secondary kinase genotypes correlate with the biological and clinical activity of sunitinib in imatinib resistant gastrointestinal stromal tumor. J Clin Oncol. 2008;26(33):5352-5359.
Hofmann, et al. Overexpression of the KIT-SCF in Uveal Melanoma Does Not Translate into Clinical Efficacy of Imatinib. Clin Cancer Res. 2009;15(1):324-329.
Hong, et al. Clinical and prognostic significances of nucelar and cytoplasmic KIT expressions in bile duct carcinomas. Modem Pathology. 2007;20:562-569.
Hsia, et al. Relationship between chemotherapy response of small cell lung cancer and P-glycoprotein or multidrug resistance-related protein expression. Lung. 2002;180(3):173-9.
Hu, et al. Thymidylate synthase expression predicts the response to 5-fluorouracil-based adjuvant therapy in pancreatic cancer. Clin Cancer Res. 2003;9(11):4165-71.

Hua, et al. Thymidylate synthase and thymidine phosphorylase gene expression as predictive parameters for the efficacy of 5-fluorouracil-based adjuvant chemotherapy for gastric cancer. World J Gastroenterol. 2007;13(37):5030-4.
Hugh, et al. Breast cancer subtypes and response to docetaxel in node-positive breast cancer: use of an immunohistochemical definition in the BCIRG 001 trial. J Clin Oncol. 2009;27(8):1168-76.
Hwang, et al. ERCC1 expression as a prognostic marker in N2(+) nonsmall-cell lung cancer patients treated with platinum-based neoadjuvant concurrent chemoradiotherapy. Cancer. 2008;113(6):1379-86.
Johnston, et al. Thymidylate synthase expression and response to neoadjuvant chemotherapy in patients with advanced head and neck cancer. J Natl Cancer Inst. 1997;89(4):308-13.
Kalinksy, et al. PIK3CA mutation associates with Improved Outcome in Breast Cancer. Clin Cancer Res. 2009;15(16):5049-5059.
Kigawa, et al. Topoisomerase-I activity and response to second-line chemotherapy consisting of camptothecin-11 and cisplatin in patients with ovarian cancer. Int J Cancer. 1999;84(5):521-4.
Kim, et al. Expression of breast cancer resistance protein is associated with a poor clinical outcome in patients with small-cell lung cancer. Lung Cancer. 2009;65(1):105-11.
Kindler, et al. Efficacy and safety of imatinib in adult pts with CKIT positive AML. Blood. 2004;103(10):3644-3654.
Kovacs, et al. MGMT immunoexpression predicts responsiveness of pituitary tumors to temozolomide therapy. Acta Neuropathol. 2008;115(2):261-2.
Kulkarni, et al. TLE3 as a candidate biomarker of response to taxane therapy. Breast Cancer Research. 2009;11(2):1-10.
Kulke, et al. 06-Methylguanine DNA Methyltransferase Deficiency and Response to Temozolomide-Based Therapy in Patients with Neuroendocrine Tumors. Clin Cancer Res. 2009;15(1):338-345.
Kwon, et al. Prognostic value of expression of ERCC1, thymidylate synthase, and glutathione S-transferase P1 for 5-fluorouracil/oxaliplatin chemotherapy in advanced gastric cancer. Ann Oncol. 2007;18(3):504-9.
Lee, et al. Expression of ERCC1 proteins predicts poor outcome in pts with SCLC_platinum-based doublets. Lung Cancer. 2008;59:95-104.
Lenz, et al. p53 point mutations and thymidylate synthase messenger RNA levels in disseminated colorectal cancer: an analysis of response and survival. Clin Cancer Res. 1998;4(5):1243-50.
Levin, et al. Progressive low-grade oligodendrogliomas: response to temozolomide and correlation between genetic profile and O6-methylguanine DNA methyltransferase protein expression. Cancer. 2006;106(8):1759-65.
Liedtke, et al. PIK3CA activating mutations and chemotherapy sensitivity in stage II-III breat cancer. 2008;10(2):1-10.
Lim, et al. Molecular analysis of secondary kinase mutations in imatinib-resistant gastrointestinal stromal tumors. Med Oncol. 2008;25(2):207-13.
Lindardou, et al. Assessment of somatic k-RAS mutations as a mechanism associated with resistance to EGFR-targeted agents: a systematic review and meta-analysis of studies in advanced non-small-cell lung cancer and metastatic colorectal cancer. Lancet Oncol. 2008;9:962-72.
Link, et al. Thymidylate synthase quantitation and in vitro chemosensitivity testing predicts responses and survival of patients with isolated nonresectable liver tumors receiving hepatic arterial infusion chemotherapy. Cancer. 2000;89(2):288-96.
Liu, et al. Activating Mutations of N- and K-ras in Multiple Myeloma Show Different Clinical Associations: Analysis of the Eastern Cooperative Oncology Group Phase III Trial. Blood. 1996;88(7):2699-2706.
Massarelli, et al. KRAS mutation is an important predictor of resistance to therapy with epidermal growth factor receptor tyrosine kinase inhibitors in non-small-cell lung cancer. Clin Cancer Res. 2007;13(10):2890-6.
Mellinghoff, et al. Molecular determinants of the response of glioblastomas to EGFR kinase inhibitors. N Engl J Med. 2005;353(19):2012-24.

(56) References Cited

OTHER PUBLICATIONS

Miller, et al. Molecular characteristics of bronchioloalveolar carcinoma and adenocarcinoma, bronchioloalveolar carcinoma subtype, predict response to erlotinib. J Clin Oncol. 2008;26(9):1472-8.
Minckwitz, et al. Clinical response after two cycles compared to HER2, Ki-67, p53, and bcl-2. Breast Cancer Res. 2008;10(2):1-11.
Molina, et al. NH2-terminal Truncated HER-2 Protein but not Full-Length Receptor Is Associated with Nodal Metastasis in Human Breast Cancer. Clinical Cancer Research. Feb. 2002;8;347-353.
Nagata, et al. PTEN activation contributes to tumor inhibition by trastuzumab, and loss of PTEN predicts trastuzumab resistance in patients. Cancer Cell. 2004;6(2):117-27.
Nakahira, et al. Involvement of ribonucleotide reductase M1 subunit overexpression in gemcitabine resistance of human pancreatic cancer. Int J Cancer. 2007;120(6):1355-63.
Nakano, et al. Evaluations of biomarkers associated with 5-FU sensitivity for non-small-cell lung cancer patients postoperatively treated with UFT. Br J Cancer. 2006;95(5):607-15.
Naniwa, et al. Genetic diagnosis for chemosensitivity with drug-resistance genes in epithelial ovarian cancer. Int J Gynecol Cancer. 2007;17(1):76-82.
Ohsawa, et al. Immunohistochemical expression of multidrug resistance proteins as a predictor of poor response to chemotherapy and prognosis in patients with nodal diffuse large B-cell lymphoma. Oncology. 2005;68(4-6):422-31.
Paradiso, et al. Thymidylate synthase and p53 primary tumour expression as predictive factors for advanced colorectal cancer patients. Br J Cancer. 2000;82(3):560-7.
Penault-Llorca, et al. Ki67 Expression and Docetaxel Efficacy in Patients With Estrogen Receptor—Positive Breast Cancer. J Clin Oncol. 2009;27(17):2809-2815.
Penson, et al. Expression of multidrug resistance-1 protein inversely correlates with paclitaxel response and survival in ovarian cancer patients: a study in serial samples. Gynecol Oncol 2004;93(1):98-106.
Perez-Tenorio, et al. PIK3CA Mutations and PTEN Loss Correlate with Similar Prognostic Factors and Are Not Mutually Exclusive in Breast Cancer. Clinical Cancer Research. Jun. 2007;13(12):3577-3584.
Personeni, et al. Clinical usefulness of EGFR gene copy number as a predictive marker in colorectal cancer patients treated with cetuximab: a fluorescent in situ hybridization study. Clin Cancer Res. 2008;14(18):5869-76.
Popat, et al. A prospective, blinded analysis of thymidylate synthase and p53 expression as prognostic markers in the adjuvant treatment of colorectal cancer. Ann Oncol. 2006;17(12):1810-7.
Press, et al. HER-2 gene amplification, HER-2 and epidermal growth factor receptor mRNA and protein expression, and lapatinib efficacy in women with metastatic breast cancer. Clin Cancer Res. 2008;14(23):7861-70.
Raefsky, et al. Phase II study of neoadjuvant bevacizumab and trastuzumab administered with albumin-bound paclitaxel (nab paclitaxel) and carboplatin in HER2+ locally advanced breast cancer. J Clin Oncol. 2008;suppl;abstract 627.
Raspollini, et al. Increased cyclooxygenase-2 (COX-2) and P-glycoprotein-170 (MDR1) expression is associated with chemotherapy resistance and poor prognosis. Analysis in ovarian carcinoma patients with low and high survival. Int J Gynecol Cancer. 2005;15(2):255-60.
Rieger, et al. Efficacy and tolerability of alemtuzumab (CAMPATH-1H) in the salvage treatment of B-cell chronic lymphocytic leukemia—change of regimen needed? Leuk Lymphoma. 2004;45(2):345-9.
Rosell, et al. Gene expression as a predictive marker of outcome in stage IIB-IIIA-IIIB non-small cell lung cancer after induction gemcitabine-based chemotherapy followed by resectional surgery. Clin Cancer Res. 2004;10:4215s-4219s.
Rudas, et al. Expression of MRP1, LRP and Pgp in breast carcinoma patients treated with preoperative chemotherapy. Breast Cancer Res Treat. 2003;81(2):149-57.
Saal, et al. PIK3CA mutations correlate with hormone receptors, node metastatis and ErbB2, and are mutatually Exclusive with PTEN Loss in Human Breast Carcinoma. Cancer Res. 2005;65(7):2554-2559.
Saez, et al. A truncated Her2 ectodomain is inversely associated with lymph node metastasis in breast cancer. Proc Am Soc Clin Oncol 20: 2001 (abstract 139) http://www.asco.org/portal/site/ASCOv2/template.RAW/menuitem.alc60e38cd6d5b9f01 . . . Oct. 27, 2009.
Saez, et al. p95HER2 predicts worse outcome in patients with HER2 positive breast cancer. Clin Cancer Res. 2006;12(2):424-431.
Sartore-Bianchi, et al. PIK3CA mutations in colorectal cancer are associated with clinical resistance to EGFR-targeted monoclonal antibodies. Cancer Res. 2009;69(5):1851-7.
Scaltriti, et al. Expression of p95HER2, a truncated form of the HER2 receptor and response to anti-HER2 therapies in breast cancer. J Natl Cancer Inst. 2007;99:628-638.
Seidman, et al. Weekly trastuzumab and paclitaxel therapy for metastatic breast cancer with analysis of efficacy by HER2 inununophenotype and gene amplification. J Clin Oncol. 2001;19(10):2587-95.
Sevinc, et al. The diagnosis of ckit negative GIST by PDGFRA Staining: Clinical, Pathological, and Nuclear Medicine Perspective. Onkologie. 2007;30:645-648.
Sjostrom, et al. Predictive value of p53, mdm-2, p21. and mib-1 for chemotherapy response in advanced breast cancer. Clin Cancer Res. 2000;6:3101-3110.
Smyth, et al. Antiestrogen therapy is active in selected ovarian cancer cases: the use of letrozole in estrogen receptor-positive patients. Clin Cancer Res. 2007;13(12):3617-22.
Souglakos, et al. Prognostic and predictive value of common mutations for treatment response and survival in patients with metastatic colorectal cancer. British Journal of Cancer. 2009;101:465-472.
Stemke-Hale, et al. An Integrative Genomic and Proteomic Analysis of PIK3CA, PTEN and AKT mutations in Breast Cancer. Cancer Res. 2008;68(15):6084-6091.
Stendahl, et al. High progesterone receptor expression correlates to the effect of adjuvant tamoxifen in premenopausal breast cancer patients. Clin Cancer Res. 2006;12(15):4614-18.
Stuart, et al. A Randomized Phase III Cross-over Study of Tamoxifen versus Megestrol Acetate in Advanced and Recurrent Breast Cancer. Eur J Cancer. 1996;32A (11):1888-1892.
Stuart-Harris, et al. Proliferation markers and survival in early breast cancer: a systematic review and meta-analysis of 85 studies in 32,825 patients. The Breast. 2008;17:323-334.
Thurlimann, et al. Formestane versus Megestrol Acetate in Postmenopausal Breast Cancer Patients After Failure of Tamoxifen: A Phase III Prospective Randomised Cross Over Trial of Second-line Hormonal Treatment (SAKK 20/90). E J Cancer. 1997;33 (7):1017-1024.
Tinari, et al. Changes of topoIIalpha expression in breast tumors after neoadjuvant chemo predicts relapse-free survival. Clin Cancer Res. 2006;12(15):1501-1506.
Tiseo, et al. Predictors of gefitinib outcomes in advanced non-small cell lung cancer (NSCLC): Study of a comprehensive panel of molecular markers. Lung Cancer. 2010;67(3):355-60.
Toi, et al. Lapatinib monotherapy in patients with relapsed, advanced, or metastatic breast cancer: efficacy, safety, and biomarker results from Japanese patients phase II studies. British J of Cancer. 2009;101:1676-1682.
Toi, et al. Predictive implications of nucleoside metabolizing enzymes in premenopausal women with node-positive primary breast cancer who were randomly assigned to receive tamoxifen alone or tamoxifen plus tegafur-uracil as adjuvant therapy. Int J Oncol. 2007;31(4):899-906.
Van Agthoven, et al. Relevance of Breast Cancer Antiestrogen Resistance Genes in Human Breast Cancer Progression and Tamoxifen Resistance. J Clin Oncol. 2009;27(4):542-549.
Viale, et al. Chemoendocrine compared with endocrine adjuvant therapies for node-negative breast cancer: predictive value of centrally reviewed expression of estrogen and progesterone receptors—International Breast Cancer Study Group. J Clin Oncol. 2008;26(9):1404-10.

(56) References Cited

OTHER PUBLICATIONS

Viale, et al. Prognostic and Predictive Value of Centrally Reviewed Ki-67 Labeling Index in Postmenopausal Women With Endocrine-Responsive Breast Cancer: Results From Breast International Group Trial 1-98 Comparing Adjuvant Tamoxifen With Letrozole. J. Clin Oncol. 2008;26(34):5569-5575.
Viola, et al. Phase II trial of high dose imatinib in recurrent GBM with PDGFR expression. Journal of Oncology. 2007;25(18):1-1. (abstract 2056).
Warnakulasuriya, et al. p53 and P-glycoprotein expression are significant prognostic markers in advanced head and neck cancer treated with chemo/radiotherapy. J Pathol. 2000;191(1):33-38.
Woodman, et al. Activity of Dasatinib against L576P KIT mutant melanoma: Molecular, cellular, and clinical correlates. Mol Cancer Ther. 2009;8(8):2079-85.
Xia, et al. Lapatinib antitumor activity is not dependent upon phosphatase and tensin homologue deleted on chromosome 10 in ErbB2-overexpressing breast cancers. Cancer Res. 2007;67(3):1170-75.
Yamashita, et al. Immunohistochemical evaluation of hormone receptor status for predicting response to endocrine therapy in metastatic breast cancer. Breast Cancer. 2006;13(1):74-83.
Yardley, et al. Phase II study of neoadjuvant gemcitabine, epirubicin, and albumin-bound nab paclitaxel (GEA) in locally advanced breast cancer with SPARC tumor assessments. J Clin Oncol. May 20 suppl; abstract 603, 2008. 26.
Yeh, et al. Comparison of chemotherapy response with P-glycoprotein, multidrug resistance-related protein-1, and lung resistance-related protein expression in untreated small cell lung cancer. Lung. 2005;183(3):177-83.
Yoh, et al. Breast cancer resistance protein impacts clinical outcome in platinum-based chemotherapy for advanced non-small cell lung cancer. Clin Cancer Res. 2004;10(5):1691-1697.
Yu, et al. Thymidylate synthase predicts for clinical outcome in invasive breast cancer. Histol Histopathol. 2005;20(3):871-878.
Zaucha, et al. Long-term survival of a patient with primarily chemoresistant metastatic breast cancer treated with medroxyprogesterone acetate. The Breast. 2004;13:321-324.
Dumur et al., Evaluation of quality-control criteria for microarray gene expression analysis, Clin. Chemistry, 2004 50(11): 1994-2002.
International search report dated Feb. 24, 2011 for PCT Application No. US10/54366.
Jahanzeb, Adjuvant trastuzumab therapy for HER2-positive breast cancer, Clin. Breast Cancer, Aug. 2008; 8(4): 324-333.
Search report dated Jun. 14, 2010 for Singapore Application No. 1546894.
Search report dated Dec. 14, 2010 for Canadian Application No. 2651995.
Search report dated May 10, 2011 for Russian Application No. 2008146868; English translation at pp. 7, 8.
Search report dated May 30, 2011 for Singapore Application No. 1546894.
Search report dated Aug. 12, 2011 for Japanese Application No. 2007-783950; English translation at pp. 4-8.
Search report dated Dec. 2, 2011 for U.S. Appl. No. 12/658,770.
Von Hoff et al., Pilot study using molecular profiling of patients' tumors to find potential targets and select treatments for their refractory cancers, J Clin Oncol, 2010 28(33): 4877-4883.
Von Hoff et al., Pilot study using molecular profiling of patients' tumors to find potential targets and select treatments for their refractory cancers, Table A1. Pairings of Targets and Drugs, J Clin Oncol, 2010 28(33): available at http://jco.ascopubs.org/content/28/33/4877.full, accessed Dec. 16, 2011.
Von Hoff et al., Pilot study using molecular profiling of patients' tumors to find potential targets and select treatments for their refractory cancers, Table A2. Targets Noted in Patients' Tumors, Treatment Suggested on the Basis of These Results, and Treatment Investigator Would Use if No Target Was Identified (in patients with PFS ratio ≥ 1.3), J Clin Oncol, 2010 28(33): available at http://jco.ascopubs.org/content/28/33/4877.full, accessed Dec. 16, 2011.
Von Hoff et al., Pilot study using molecular profiling of patients' tumors to find potential targets and select treatments for their refractory cancers, Table A3. Targets Noted in Patients' Tumors, Treatment Suggested on the Basis of These Results, and Treatment Investigator Would Use if No Target Was Identified (in patients with PFS ratio < 1.3), J Clin Oncol, 2010 28(33): available at http://jco.ascopubs.org/content/28/33/4877.full, accessed Dec. 16, 2011.
Evans et al. Pharmacogenomics: translating functional genomics into rational therapeutics. Science. 1999; 286: 487-91.
International preliminary report on patentability dated Aug. 16, 2011 for PCT Application No. US2010/000407.
Sadee et al. Pharmacogenetics/genomics and personalized medicine. Human Molecular Genetics. 2005; 14: 207-14.
Search report dated Dec. 5, 2011 for European Application No. 07783950.4.
Search report dated Feb. 29, 2012 for Canadian Application No. 2651995.
Shastry. Pharmacogenetics and the concept of individualized medicine. Pharmacogenomics Journal. 2006; 6: 16-21.
Adlard et al. Prediction of the response of colorectal cancer to systemic therapy. Lancet Oncology. 2002; 3: 75-82.
Brueckner et al. DNA methyltransferase inhibitors: old and new drugs for an epigenetic cancer therapy. TRENDS in Pharmacol Sciences. 2004; 25: 551-554.
Chan et al. CpG island methylation in carcinoid and pancreatic endocrine tumors. Oncogene (2003) 22, 924-934.
Chappuis et al. A significant response to neoadjuvant chemotherapy in BRCA 1/2 related breast cancer. J Med Genet. 2002; 39: 608-610.
Chekerov et al. Altered expression pattern of topoisomerase II$\alpha$ in ovarian tumor epithelial and stromal cells after platinum-based chemotherapy. Neoplasia. 2006; 1: 38-45.
Dumur et al. Evaluation of quality-control criteria for microarray gene expression analysis. Clin. Chemistry. 2004; 50(11): 1994-2002.
Duxbury et al. RNA interference targeting the M2 subunit of ribonucleotide reductase enhances pancreatic adenocarcinoma chemosensitivity to gemcitabine. Oncogene. 2004; 23: 1539-1548.
Fjallskog et al. Expression of Molecular Targets for Tyrosine Kinase Receptor Antagonists in Malignant Endocrine Pancreatic Tumors. Clinical Cancer Research. 2003; 9: 1469-1473.
Giovannetti et al. Transcription analysis of human equilibrative nucleoside transporter-1 predicts survival in pancreas cancer patients treated with gemcitabine. Cancer Res. 2006; 66: 3928-3935.
Gyurkocza et al. Antileukemic activity of shepherdin and molecular diversity of Hsp90 inhibitors. Journal of The National Cancer Institute. 2006; 98(15): 1068-1077.
Hernandez-Vargas et al. Transcriptional profiling of MCF7 breast cancer cells in responseto 5-Fluorouracil: Relationship with cell cycle changes and apoptosis, and identification of novel targets of p53. Int. J. Cancer. 2006; 119: 1164-1175.
Jahanzeb. Adjuvant trastuzumab therapy for HER2-positive breast cancer, Clin. Breast Cancer, Aug. 2008; 8(4): 324-333.
Kabbinavar et al. Phase II, randomized trial comparing bevacizumab plus fluorouracil (FU)/leucovorin (LV) with FU/LV alone in patients with metastatic colorectal cancer. Journal of Clinical Oncology. 2003; 21: 60-65.
Kon et al. Tissue microarray. Molecular Medicine. 2001; 38(7): 825-828; English translation at pp. 8-20.
Kubota et al. Identification of somatostatin receptor subtypes and an implication for the efficacy of somatostatin analogue SMS 201-995 in treatment of human endocrine tumors. J. Clin. Invest. 1994; 93: 1321-1325.
Lin et al. Epha2 overexpression is associated with angiogenesis in ovarian cancer. Cancer. 2007; 109: 332-340.
Lundin et al. Cellular immune reconstitution after subcutaneous alemtuzumab (anti-CD52 monoclonal antibody, CAMPATH-1 H) treatment as first-line therapy for B-cell chronic lymphocytic leukaemia. Leukemia. 2004; 18: 484-490.
Office Action for U.S. Appl. No. 12/658,770 mailed Dec. 5, 2011.
Office Action for U.S. Appl. No. 12/658,770 mailed Aug. 31, 2012.
Office Action for U.S. Appl. No. 12/658,770 mailed Jun. 19, 2013.
Office Action for U.S. Appl. No. 13/188,350 mailed Jun. 19, 2013.
Paduano et al. Silencing of survivin gene by small interfering RNAs produces supra-additive growth suppression in combination with

(56) References Cited

OTHER PUBLICATIONS 17-allylamino-17-demethoxygeldanamycin in human prostate cancer cells. Mol Cancer Ther. 2006; 5(1): 179-186.
Patent allowance dated Jul. 31, 2013 for Chinese Application No. 200780018015.9.
Robles-Diaz et al. Pancreas: A sex steroid-dependent tissue. IMAJ. 2001; 3:364-368.
Scholl et al. Targeting HER2 in other tumor types. Annals of Oncology. 2001; 12 (Suppl. 1): S81-S87.
Search report dated Feb. 13, 2012 for Chinese Application No. 200780018015.9.
Search report dated Apr. 5, 2012 for Australian Application No. 2007253740.
Search report dated Apr. 13, 2012 for Mexican Application No. MX/a/2008/014608. English translation at pp. 3-4 (attorney comment redacted).
Search report dated Apr. 18, 2012 for Singapore Application No. 200808439-4.
Search report dated Apr. 26, 2012 for European Application No. 2009821173.
Search report dated May 29, 2012 for Israeli Application No. 195266. English translation at pp. 6-11 (attorney comment redacted).
Search report dated Aug. 21, 2012 for Japanese Application No. 2009511252; English translation at pp. 5-11.
Search report dated Dec. 3, 2012 for Chinese Application 200980148416.5.
Search report dated Feb. 4, 2013 for Canadian Application No. 2,651,995.
Search report dated Feb. 6, 2013 for Chinese Application No. 200780018015.9.
Search report dated Apr. 4, 2013 for Israeli Application No. 212349.
Search report dated Jul. 5, 2013 for Korean Application No. 10-2008-7028343.
Search report dated Jul. 9, 2013 for Indian Application No. 4619/KOLNP/2008.
Taron et al. BRCA 1 mRNA expression levels as an indicator of chemoresistance in lung cancer. Human Mol Genet. 2004; 13: 2443-2449.
Teng et al. Can inhibition of telomerase increase pancreatic cancer cell's susceptibility to chemotherapeutic reagents? Hepatobiliary Pancreat Dis Int. 2002; 1:155-160.
Wolf et al. Science, medicine, and the future: pharmacogenetics. BMJ. 2000; 320: 987-990.
Yoshida. Anti-cancer drugs targeting cancer-related gene products. Gekkan Soshiki Baiyo Kogaku. 2001; 27(6): 238-241; English translation at pp. 6-17.
Zent et al. The distinct gene expression profiles of chronic lymphocytic leukemia and multiple myeloma suggest different anti-apoptotic mechanisms but predict only some differences in phenotype. Leukemia Research. 2003; 27: 765-774.

* cited by examiner

| MOLECULAR PROFILING INSTITUTE | PATIENT INFORMATION<br>NAME: SAMPLE PATIENT<br>SEX: FEMALE<br>DOB: 6/1/1974<br>SSN#: 123-45-6789 | PHYSICIAN INFORMATION<br>SOME DOCTOR, M.D.<br>1234 E. SOUTH ST.<br>TUCSON, AX 12345<br>480-123-4567 |
|---|---|---|
| | REPORT INFORMATION VER 1.6.2:4-25-06<br>DATE SPECIMEN RECEIVED: 02/01/2006  DATE REPORTED: 02/09/2006  CASE NO. MP-TN06-05040<br>DATE SPECIMEN COLLECTED AT HOST MEDICAL CENTER: 01/24/2006 | |

| SPECIAL STUDIES |
|---|
| RESULTS AND INTERPRETATION |

INTERPRETATION:

REVIEW OF PATHOLOGY SLIDES: (RECEIVED FROM MAIN HOSPITAL, TUCSON, AZ, ONE PARAFFIN BLOCK LABELED M01-123 AND FROZEN TISSUE).

PELVIC AND RETROPERITONEAL TUMOR: INFLAMMATORY MYOFIBROLASTIC TUMOR.

POSSIBLE AGENTS THAT MIGHT INTERACT WITH CANDIDATE GENE TARGETS:

| ASSAY* | CANDIDATE TARGET | SIGNIFICANT RESULT | POSSIBLE AGENT(S) |
|---|---|---|---|
| MICROARRAY | NFKBIA | (INCREASED 1.78)** | VELCADE |
| IHC | C-KIT | (INCREASED +2, 90%) | GLEEVEC, SUTENT |
| MICROARRAY | PDGFRA | (INCREASED 4.74)** | GLEEVEC, SORAFENIB, SUTENT |
| MICROARRAY | GART | (INCREASED 1.90)** | ALIMTA |
| MICROARRAY | VDR | (INCREASED 37.30)** | CALCITRIOL |
| MICROARRAY | ADA | (INCREASED 5.26)** | PENTOSTATIN |
| MICROARRAY | TOP1 | (INCREASED 2.78)** | TOPOTECAN, CAMPTOSAR (CPT11) |
| MICROARRAY | HIF1A | (INCREASED 4.03)** | AVASTIN, SORAFENIB, SUTENT |
| MICROARRAY | DNMT1 | (INCREASED 1.51)** | VIDAZA (5-AZACYTIDINE) |

*IHC = IMMUNOHISTOCHEMISTRY
** INCREASED OR DECREASED ARE RELATIVE TO NORMAL CONTRLS.

FIG.3A

| MOLECULAR PROFILING INSTITUTE | PATIENT INFORMATION<br>NAME: SAMPLE PATIENT<br>SEX: FEMALE<br>DOB: 6/1/1974<br>SSN#: 123-45-6789 | PHYSICIAN INFORMATION<br>SOME DOCTOR, M.D.<br>1234 E. SOUTH ST.<br>TUCSON, AX 12345<br>480-123-4567 |
|---|---|---|
| | REPORT INFORMATION VER 1.6.2:4-25-06<br>DATE SPECIMEN RECEIVED: 02/01/2006 DATE REPORTED: 02/09/2006 CASE NO. MP-TN06-05040<br>DATE SPECIMEN COLLECTED AT HOST MEDICAL CENTER: 01/24/2006 | |

SPECIAL STUDIES
RESULTS AND INTERPRETATION

ADVANCED IMMUNOHISTOCHEMICAL ANALYSIS:

| GENE EXPRESSED PROTEIN | CONCLUSION | SPECIFICITY | INTENSITY | % | TARGET STATUS* |
|---|---|---|---|---|---|
| HER2/NEU | NEGATIVE | | | | |
| ER | NEGATIVE | | | | |
| PR | NEGATIVE | | | | |
| C-KIT | POSITIVE | SPECIFIC | 2 | 90 | TARGET |
| EGFR | NEGATIVE | | | | |
| COX-2 | NEGATIVE | | | | |
| ANDROGEN RECEPTOR | NEGATIVE | | | | |
| CD52 | NEGATIVE | | | | |
| PDGFR | NEGATIVE | NON-SPECIFIC | | | |
| CD25 | NEGATIVE | | | | |

* 2+ IHC IN GREATER THAN 30% OF THE TUMOR CELLS HAS BEEN CHOSEN AS A CONSERVATIVE DIVIDING POINT TO REPORT A POTENTIAL TARGET AS POSITIVE TO HELP INCREASE PHARMACOLOGIC EFFECTIVENESS.

IMMUNOHISTOCHEMICAL TESTS NOT PERFORMED

| | | |
|---|---|---|
| IL-2 | TOPOISOMERASE I | MLH1 |
| NF-KAPPA BETA | TOPOISOMERASE II | MSH2 |
| THYMIDYLATE SYNTHASE | RETINOIC ACID RECEPTOR | CD20 |
| ERCC3 (HELICASE) | R X R | P53 |
| THYMIDINE PHOSPHORYLASE | ORNITHINE DECARBOXYLASE | CYCLIN D1 |
| NGF | SOMATOSTATIN | BCL-2 |
| MTAP | RAS (MUTATED) | VEGF |
| MAP KINASE PROTEIN | ASPARAGINE SYNTHETASE | |
| XANTHINE OXIDASE | | |

FIG.3B

MOLECULAR PROFILING INSTITUTE

| PATIENT INFORMATION | PHYSICIAN INFORMATION |
|---|---|
| NAME: SAMPLE PATIENT | SOME DOCTOR, M.D. |
| SEX: FEMALE | 1234 E. SOUTH ST. |
| DOB: 6/1/1974 | TUCSON, AX 12345 |
| SSN#: 123-45-6789 | 480-123-4567 |

REPORT INFORMATION VER 1.6.2:4-25-06
DATE SPECIMEN RECEIVED: 02/01/2006   DATE REPORTED: 02/09/2006   CASE NO. MP-TN06-05040
DATE SPECIMEN COLLECTED AT HOST MEDICAL CENTER: 01/24/2006

SPECIAL STUDIES
MICROARRAY RESULTS

MICROARRAY ANALYSIS:

| GENE | RATIO | EXPRESSION* ANALYSIS | GENE | RATIO | EXPRESSION* ANALYSIS | GENE | RATIO | EXPRESSION* ANALYSIS |
|---|---|---|---|---|---|---|---|---|
| AR | 0.02 | UNDER EXPRESSED | EGFR | 1.16 | NO CHANGE | ZAP70 | 3.00 | NO CHANGE |
| ESR1 | 0.09 | UNDER EXPRESSED | OGFR | 1.17 | NO CHANGE | ZAP70 | 3.02 | NO CHANGE |
| PGR | 0.10 | UNDER EXPRESSED | MLH1 | 1.19 | NO CHANGE | CD33 | 3.05 | OVER EXPRESSED |
| VEGF | 0.33 | UNDER EXPRESSED | VHL | 1.22 | NO CHANGE | ZAP70 | 3.06 | NO CHANGE |
| KIT | 0.51 | UNDER EXPRESSED | TNF | 1.29 | NO CHANGE | ZAP70 | 3.13 | NO CHANGE |
| PDGFC | 0.53 | UNDER EXPRESSED | RARA | 1.38 | NO CHANGE | ZAP70 | 3.18 | NO CHANGE |
| RXRB | 0.62 | NO CHANGE | HSPCA | 1.42 | NO CHANGE | ZAP70 | 3.40 | NO CHANGE |
| TOP2B | 0.62 | UNDER EXPRESSED | TXNRD1 | 1.42 | NO CHANGE | CD33 | 3.52 | OVER EXPRESSED |
| RAF1 | 0.68 | NO CHANGE | ASNS | 1.44 | NO CHANGE | HIF1A | 3.84 | OVER EXPRESSED |
| ERBB2 | 0.69 | NO CHANGE | DNMT1 | 1.51 | OVER EXPRESSED | HIF1A | 3.85 | OVER EXPRESSED |
| ERCC3 | 0.71 | NO CHANGE | NFKB2 | 1.74 | NO CHANGE | HIF1A | 3.88 | OVER EXPRESSED |
| BCL2 | 0.71 | NO CHANGE | NFKBIA | 1.78 | OVER EXPRESSED | HIF1A | 3.90 | OVER EXPRESSED |
| PDGFRB | 0.78 | NO CHANGE | PTGS2 | 1.81 | NO CHANGE | HIF1A | 3.90 | OVER EXPRESSED |
| BCL2 | 0.80 | NO CHANGE | BRCA2 | 1.83 | NO CHANGE | HIF1A | 3.91 | OVER EXPRESSED |
| GSTP1 | 0.85 | NO CHANGE | GART | 1.90 | OVER EXPRESSED | HIF1A | 3.94 | OVER EXPRESSED |
| SPARC | 0.92 | NO CHANGE | CDW52 | 2.15 | OVER EXPRESSED | HIF1A | 3.97 | OVER EXPRESSED |
| HDAC1 | 0.95 | NO CHANGE | ZAP70 | 2.18 | NO CHANGE | HIF1A | 4.01 | OVER EXPRESSED |
| POLA | 0.98 | NO CHANGE | FOLR2 | 2.21 | OVER EXPRESSED | HIF1A | 4.03 | OVER EXPRESSED |
| MSH2 | 0.98 | NO CHANGE | ZAP70 | 2.76 | NO CHANGE | PDGFRA | 4.74 | OVER EXPRESSED |
| CES2 | 1.05 | NO CHANGE | TOP1 | 2.78 | OVER EXPRESSED | TK1 | 4.94 | OVER EXPRESSED |
| VEGF | 1.09 | NO CHANGE | MS4A1 | 2.86 | NO CHANGE | IL2RA | 5.07 | NO CHANGE |
| SSTR1 | 1.11 | NO CHANGE | ZAP70 | 2.86 | NO CHANGE | ADA | 5.26 | OVER EXPRESSED |
| PTEN | 1.11 | NO CHANGE | ZAP70 | 2.92 | NO CHANGE | TOP2A | 9.34 | NO CHANGE |
| | | | | | | TYMS | 22.95 | OVER EXPRESSED |
| | | | | | | VDR | 37.30 | OVER EXPRESSED |

*"NO CHANGE" INDICATES THAT THERE IS NO DIFFERENCE IN EXPRESSION FOR THIS GENE BETWEEN THE TUMOR AND CONTROL TISSUES AT A SIGNIFICANCE LEVEL OF P<=0.001. A SIGNIFICANCE LEVEL OF P<=0.001 HAS BEEN CHOSEN SINCE GENES PASSING THIS THRESHOLD CAN BE VALIDATED AS DIFFERENTIALLY EXPRESSED BY ALTERNATIVE METHODS APPROXIMATELY 95% OF THE TIME.

FIG.3C

PATIENT: SAMPLE PATIENT                CASE NO. MP-TN06-05040                DATE REPORTED: 2/9/2006

100

| CLINICAL INFORMATION |
|---|

CLINICAL HISTORY
  THE PATIENT WAS DIAGNOSED WITH INFLAMATORY MYOFIBROBLASTIC TUMOR IN FEB, 2004. AT THAT TIME A LARGE
  MASS WAS REMOVED FROM HER ABDOMEN. THE PATIENT NOW HAS RECURRENT MASSES ON HER LEFT UPPER QUADRANT
120 AND IN THE PELVIS. PER THE PATIENT CHART, DR SOME REVIEWED THIS CASE WITH DR VON HOFF AND IT WAS AGREED
  THAT PERFORMING DNA MICROARRAY AND IHC TESTING ON THIS PATIENT MAY PROVIDE INSIGHT INTO FURTHER TREATMENT
  OPTIONS.

SPECIMENS SUBMITTED
  RECEIVED FROM MAIN HOSPITAL, TUCSON, AZ, ONE PARAFFIN BLOCK LABELED M01-123 AND FROZEN TISSUE WITH THE
  ACCOMPANYING SURGICAL PATHOLOGY REPORT.
122

DISCLAIMER
  THESE TESTS WERE DEVELOPED BY MOLECULAR PROFILING AND THEIR PERFORMANCE CHARACTERISTICS DETERMINED
  BY MOLECULAR PROFILING. IT HAS NOT BEEN CLEARED OR APPROVED BY THE U.S. FOOD AND DRUG ADMINISTRATION
  (FDA). THESE TESTS ARE PERMITTED FOR CLINICAL PURPOSES AND SHOULD NOT BE REGARDED AS PURELY
  INVESTIGATIONAL OR FOR RESEARCH. MOLECULAR PROFILING IS CERTIFIED UNDER THE CLINICAL LABORATORY
  IMPROVEMENT AMENDMENTS OF 1988 (CLIA) AS QUALIFIED TO PERFORM HIGH-COMPLEXITY CLINICAL TESTING.

DECISIONS REGARDING CARE AND TREATMENT SHOULD NOT BE BASED ON A SINGLE TEST SUCH AS THIS TEST. RATHER
  DECISIONS ON CARE AND TREATMENT SHOULD BE BASED ON THE INDEPENDENT MEDICAL JUDGMENT OF THE TREATING
  PHYSICIAN TAKING INTO CONSIDERATION ALL AVAILABLE INFORMATION CONCERNING THE PATIENT'S CONDITION,
  INCLUDING OTHER LABORATORY TESTS, IN ACCORDANCE WITH THE STANDARD OF CARE IN A GIVEN COMMUNITY.

THE FINDING OF A TARGET DOES NOT NECESSARILY INDICATE PHARMACOLOGIC EFFECTIVENESS.

ROBERT J. PENNY, MD, PHD, PATHOLOGIST AND MEDICAL DIRECTOR    DATE 2/9/2006

SYSTEM AND METHOD FOR DETERMINING INDIVIDUALIZED MEDICAL INTERVENTION FOR A DISEASE STATE

CROSS-REFERENCE TO RELATED APPLICATIONS

This application is a utility patent application based on provisional patent application entitled "SYSTEM AND METHOD FOR DETERMINING INDIVIDUALIZED MEDICAL INTERVENTION FOR A DISEASE STATE" and having Ser. No. 60/747,645, filed May 18, 2006, which is herein incorporated in its entirety.

FIELD OF INVENTION

The present invention generally relates to the application of molecular profiling to provide a system and method for determining medical intervention for a particular disease state. The system and method can be conducted at any stage of the disease. In particular, the present invention relates to a system and method for determining medical intervention for a seriously diseased patient, for example, a patient with cancer that has progressed on at least two chemotherapeutic or hormonal regimens, where the method includes the molecular profiling of a biological sample from the patient, determining whether any molecular findings including one or more genes, gene expressed proteins, molecular mechanisms, and/or combinations of such molecular findings exhibit a change in expression compared to a normal reference, and identifying a drug therapy capable of interacting with the genes, gene expressed proteins, molecular mechanisms, or combinations of such molecular findings that exhibited a change in expression.

BACKGROUND OF THE INVENTION

Disease states in patients are typically treated with treatment regimens or therapies that are selected based on clinical based criteria; that is, a treatment therapy or regimen is selected for a patient based on the determination that the patient has been diagnosed with a particular disease (which diagnosis has been made from classical diagnostic assays). Although the molecular mechanisms behind various disease states have been the subject of studies for years, the specific application of a diseased individual's molecular profile in determining treatment regimens and therapies for that individual has been disease specific and not widely pursued.

Some treatment regimens have been determined using molecular profiling in combination with clinical characterization of a patient such as observations made by a physician (such as a code from the International Classification of Diseases, for example, and the dates such codes were determined), laboratory test results, x-rays, biopsy results, statements made by the patient, and any other medical information typically relied upon by a physician to make a diagnosis in a specific disease. However, using a combination of selection material based on molecular profiling and clinical characterizations (such as the diagnosis of a particular type of cancer) to determine a treatment regimen or therapy presents a risk that an effective treatment regimen may be overlooked for a particular individual since some treatment regimens may work well for different disease states even though they are associated with treating a particular type of disease state.

Patients with metastatic cancer are of particular concern for treating physicians. The majority of patients with metastatic cancer eventually run out of treatment options for their tumors. These patients have very limited options after their tumor has progressed on standard front line and second line (and sometimes third line and beyond) therapies. Although these patients may participate in Phase I and Phase II clinical trials for new anticancer agents, they must usually meet very strict eligibility criteria to do so. Studies have shown that when patients participate in these types of trials, the new anticancer agent may give response rates of anywhere from 5% to 10% on average in Phase I settings to 12% in Phase II settings. These patients also have the option of electing to receive the best supportive care to treat their symptoms.

There has recently been an explosion of interest in developing new anticancer agents that are more targeted against a cell surface receptor or an up regulated or amplified gene product. This approach has met with some success (e.g. Herceptin against HER2/neu in breast cancer cells, rituximab against CD20 in lymphoma cells, bevacizamab against VEGF, Cetuximab against EGFR, etc.). However, patients' tumors still eventually progress on these therapies. If a larger number of targets or molecular findings such as molecular mechanisms, genes, gene expressed proteins, and/or combinations of such were measured in a patient's tumor, one may find additional targets or molecular findings that can be exploited by using specific therapeutic agents. Identifying multiple agents that can treat multiple targets or underlying mechanisms would provide a metastatic cancer patient with a viable therapeutic alternative to those treatment regimens which currently exist.

Accordingly, there is a need for a system and method for determining an individualized medical intervention for a disease state based on molecular profiling that is used to target specific genes and/or gene expressed proteins with specific drugs or agents that is independent of disease lineage diagnosis.

SUMMARY OF THE INVENTION

The present invention is directed to a system and method for determining individualized medical intervention for a particular disease state. One exemplary method of the present invention for determining medical intervention for a disease state includes the steps of performing a test for a gene and/or a test for a gene expressed protein from a biological sample of a diseased individual, determining which genes and/or gene expressed proteins exhibited change in expression compared to a reference, and identifying a drug therapy used to interact with the gene and/or gene expressed proteins that exhibited a change of expression that is not single disease restricted. In one aspect of this exemplary embodiment of the invention, the step of identifying a drug therapy used to interact with a gene and/or gene expressed protein that exhibited a change in expression may include the step of identifying a drug therapy from an automated review of an extensive literature database and/or data generated from clinical trials.

In another aspect of the above-described exemplary embodiment of the present invention, the step of performing a test for a gene and/or a test for a gene expressed protein may include the step of performing an immunohistochemical (IHC) analysis and/or a micro array analysis. Further, the step of performing a micro array analysis may include the step of performing an analysis using an expression micro array, a comparative genomic hybridization (CGH) micro array, a single nucleotide polymorphism (SNP) micro array, a fluorescent in-situ hybridization (ISH), an in-situ hybridization (ISH), and a proteomic array. In addition, the step of performing an IHC analysis may include the step of performing an IHC analysis for a gene expressed protein which includes at least one of Her2/Neu, ER, PR, c-kit, EGFR, MLH1, MSH2, CD20, p53, Cyclin D1, bcl2, COX-2, Androgen receptor, CD52, PDGFR, AR, CD25, and VEGF.

In another aspect of the invention, the step of performing a micro array analysis in the above-described exemplary method for determining medical intervention for a disease state may include the step of performing a micro array analysis for a gene which includes at least one of BCL2, HIF1A, AR, ESR1, PDGFRA, KIT, PDGFRB, CDW52, ZAP70, PGR, SPARC, GART, GSTP1, NFKBIA, MSH2, TXNRD1, HDAC1, PDGFC, PTEN, CD33, TYMS, RXRB, ADA, TNF, ERCC3, RAF1, VEGF, TOP1, TOP2A, BRCA2, TK1, FOLR2, TOP2B, MLH1, IL2RA, DNMT1, HSPCA, ERBR2, ERBB2, SSTR1, VHL, VDR, PTGS2, POLA, CES2, EGFR, OGFR, ASNS, NFKB2, RARA, MS4A1, DCK, DNMT3A, EREG, Epiregulin, FOLR1, GNRH1, GNRHR1, FSHB, FSHR, FSHPRH1, folate receptor, HGF, HIG1, IL13RA1, LTB, ODC1, PPARG, PPARGC1, VHL, Lymphotoxin Beta Receptor, Myc, TOP2B Topoisomerase II, TOPO2B, TXN, VEGFC, ACE2, ADH1C, ADH4, AGT, AREG, CA2, CDK2, caveolin, and NFKB1.

In yet another aspect of the above-described exemplary method of the present invention, the step of performing a test for a gene and/or a test for a gene expressed protein from a biological sample of a diseased individual may include the step of performing an immunohistochemical analysis on a tumor and the step of determining which genes and/or gene expressed proteins exhibit a change in expression compared to a reference may include the step of determining whether 30% or more of the tumor cells were +2 or greater standing for a particular gene expressed protein. In still another aspect of the above-described exemplary method of the present invention, the step of performing a test for a gene and/or a test for a gene expressed protein from a biological sample of a diseased individual may include the step of performing a micro array analysis on a tumor and the step of determining which genes and/or gene expressed proteins exhibit a change in expression compared to a reference may include the step of identifying which genes are up-regulated or down-regulated by determining whether the full change of expression for a particular gene relative to a normal tissue of origin reference is significant at $p<0.001$. Furthermore, the above-described exemplary method of the present invention for determining medical intervention for a disease state may also include the step of providing a patient profile report which identifies the change in expression for the genes and/or gene expressed proteins along with a possible drug therapy for interaction with each of the genes and/or gene expressed proteins that exhibit a change in expression.

Another exemplary embodiment of the present invention is directed to a method for identifying a drug therapy capable of interacting with a molecular target which includes the steps of identifying a molecular target in a plurality of diseased individuals that exhibits a change in expression when compared to a normal reference, administrating a drug therapy to the diseased individuals that exhibit the change in expression of the molecular target, and determining any changes in the molecular target of the diseased individuals after the drug therapy. Further, in one aspect of this exemplary embodiment of a method for identifying a drug therapy capable of interacting with the molecular target, the step of identifying a molecular target in a plurality of diseased individuals that exhibits a change in expression when compared to a normal reference may include the step of performing a test for a gene and/or a test for a gene expressed protein from a biological sample of the diseased individual where the test comprises an immunohistochemical (IHC) analysis and/or a micro array analysis.

In yet another exemplary embodiment of the present invention, a system is provided for determining individualized medical intervention for a disease state where the system includes a host server, a user interface for accessing the host server to access and input data, a processor for processing the inputted data, a memory coupled to the processor for storing the processed data and instructions for: a) accessing a molecular profile taken from a biological specimen of a patient b) determining whether at least one of a gene, a gene expressed protein, a molecular mechanism, and other molecular findings resulting from the molecular profile exhibit change in expression compared to a normal reference, and c) accessing a drug therapy database to identify one or more drug therapies that interact with a gene, a gene expressed protein, a molecular mechanism, and/or other molecular findings that exhibited a change in expression, and a display means for displaying a gene, a gene expressed protein, a molecular mechanism, and other molecular findings exhibiting a change in expression and the drug therapies that interact with them. With respect to the exemplary embodiment of the present invention directed to the system for determining individualized medical intervention for a disease state, the molecular profile taken from the biological specimen may include the same immunohistochemical (IHC) analysis and micro array analysis described above with reference to the first exemplary embodiment of the present invention. In addition, the different types of these analyses along with the genes analyzed using these analyses may be the same as those described above with reference to the first exemplary embodiment of the present invention which is directed to a method for determining medical intervention for a disease state.

Still another exemplary embodiment of the present invention is directed to a method for determining medical intervention for a disease state which includes the steps of performing at least one molecular test for at least one target from a biological sample of a diseased individual, determining whether the target exhibits a change in expression compared to a reference, and identifying at least one non-disease specific agent that interacts with the target that exhibits a change in expression. The step of identifying at least one non-diseased specific agent that interacts with the target may include the step of identifying a drug therapy from an automated review of an extensive literature base and/or an automated review of data generated from clinical trials. In addition, the exemplary embodiment of the present invention directed to a method for determining medical intervention for a disease state may also include the step of providing a patient profile report which includes the patient's test results for various targets and any proposed therapies based on those results.

The step of performing at least one molecular test for at least one target from a biological sample of a diseased individual in the exemplary embodiment of the present invention directed to a method for determining medical intervention for a disease state may include all of the above-described analyses relating to immunohistochemical (IHC) analysis and micro array analysis and the genes analyzed using those analyses.

BRIEF DESCRIPTION OF THE DRAWINGS

FIGS. 3A through 3D illustrate an exemplary patient profile report in accordance with step 80 of FIG. 2.

FIGS. 15-25 are computer screen print outs associated with various parts of the information-based personalized medicine drug discovery system and method shown in FIGS. 5-14.

DETAILED DESCRIPTION

Figure 1:
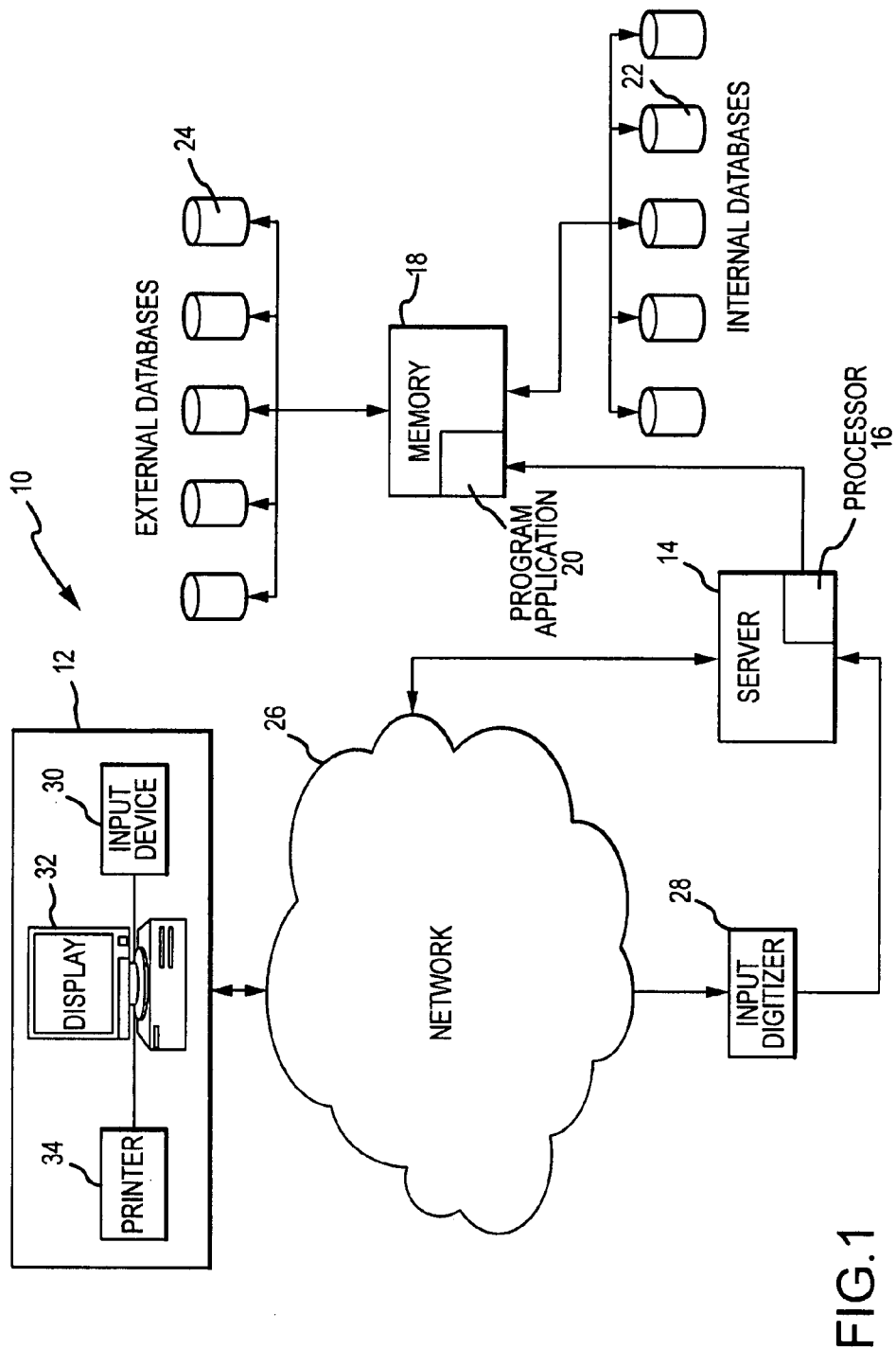
FIG. 1 illustrates a block diagram of an exemplary embodiment of a system for determining individualized medical intervention for a particular disease state that utilizes molecular profiling of a patient's biological specimen that is non disease specific.

The detailed description of exemplary embodiments herein makes reference to the accompanying drawings and pictures, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: patient data such as family history, demography and environmental data, biological sample data, prior treatment and protocol data, patient clinical data, molecular profiling data of biological samples, data on therapeutic drug agents and/or investigative drugs, a gene library, a disease library, a drug library, patient tracking data, file management data, financial management data, billing data and/or like data useful in the operation of the system. As those skilled in the art will appreciate, user computer may include an operating system (e.g., Windows NT, 95/98/2000, OS2, UNIX, Linux, Solaris, MacOS, etc.) as well as various conventional support software and drivers typically associated with computers. The computer may include any suitable personal computer, network computer, workstation, minicomputer, mainframe or the like. User computer can be in a home or medical/business environment with access to a network. In an exemplary embodiment, access is through a network or the Internet through a commercially-available web-browser software package.

As used herein, the term "network" shall include any electronic communications means which incorporates both hardware and software components of such. Communication among the parties may be accomplished through any suitable communication channels, such as, for example, a telephone network, an extranet, an intranet, Internet, point of interaction device, personal digital assistant (e.g., Palm Pilot®, Blackberry®, cellular phone, kiosk, etc.), online communications, satellite communications, off-line communications, wireless communications, transponder communications, local area network (LAN), wide area network (WAN), networked or linked devices, keyboard, mouse and/or any suitable communication or data input modality. Moreover, although the system is frequently described herein as being implemented with TCP/IP communications protocols, the system may also be implemented using IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

As used herein, "transmit" may include sending electronic data from one system component to another over a network connection. Additionally, as used herein, "data" may include encompassing information such as commands, queries, files, data for storage, and the like in digital or any other form.

The system contemplates uses in association with web services, utility computing, pervasive and individualized computing, security and identity solutions, autonomic computing, commodity computing, mobility and wireless solutions, open source, biometrics, grid computing and/or mesh computing.

Any databases discussed herein may include relational, hierarchical, graphical, or object-oriented structure and/or any other database configurations. Common database products that may be used to implement the databases include DB2 by IBM (White Plains, N.Y.), various database products available from Oracle Corporation (Redwood Shores, Calif.), Microsoft Access or Microsoft SQL Server by Microsoft Corporation (Redmond, Wash.), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In one exemplary embodiment, the ability to store a wide variety of information in different formats is facilitated by storing the information as a BLOB. Thus, any binary information can be stored in a storage space associated with a data set. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data by multiple and unrelated owners of the data sets. For example, a first data set which may be stored may be provided by a first party, a second data set which may be stored may be provided by an unrelated second party, and yet a third data set which may be stored, may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, in one exemplary embodiment, the data set (e.g., BLOB) may be annotated in a standard manner when provided for manipulating the data. The annotation may comprise a short header, trailer, or other appropriate indicator related to each data set that is configured to convey information useful in managing the various data sets. For example, the annotation may be called a "condition header", "header", "trailer", or "status", herein, and may comprise an indication of the status of the data set or may include an identifier correlated to a specific issuer or owner of the data. Subsequent bytes of data may be used to indicate for example, the identity of the issuer or owner of the data, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, issuer or owner of data, user or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate. The data, including the header or trailer may be received by a stand alone interaction device configured to add, delete, modify, or augment the data in accordance with the header or trailer.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

The computing unit of the web client may be further equipped with an Internet browser connected to the Internet or an intranet using standard dial-up, cable, DSL or any other Internet protocol known in the art. Transactions originating at a web client may pass through a firewall in order to prevent unauthorized access from users of other networks. Further, additional firewalls may be deployed between the varying components of CMS to further enhance security.

Firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based and Packet Filtering among others. Firewall may be integrated within an web server or any other CMS components or may further reside as a separate entity.

The computers discussed herein may provide a suitable website or other Internet-based graphical user interface which is accessible by users. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and the like. A server may include a web service that receives a request from a web server, the request including a URL (http://yahoo.com/stockquotes/ge) and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, XSLT, SOAP, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference.

The web-based clinical database for the system and method of the present invention preferably has the ability to upload and store clinical data files in native formats and is searchable on any clinical parameter. The database is also scalable and may utilize an EAV data model (metadata) to enter clinical annotations from any study for easy integration with other studies. In addition, the web-based clinical database is flexible and may be XML and XSLT enabled to be able to add user customized questions dynamically. Further, the database includes exportability to CDISC ODM.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, Macromedia Cold Fusion, Microsoft Active Server Pages, Java, COBOL, assembler, PERL, Visual Basic, SQL Stored Procedures, extensible markup language (XML), with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As used herein, the term "end user", "consumer", "customer", "client", "treating physician", "hospital", or "business" may be used interchangeably with each other, and each shall mean any person, entity, machine, hardware, software or business. Each participant is equipped with a computing device in order to interact with the system and facilitate online data access and data input. The customer has a computing unit in the form of a personal computer, although other types of computing units may be used including laptops, notebooks, hand held computers, set-top boxes, cellular telephones, touch-tone telephones and the like. The owner/operator of the system and method of the present invention has a computing unit implemented in the form of a computer-server, although other implementations are contemplated by the system including a computing center shown as a main frame computer, a mini-computer, a PC server, a network of computers located in the same of different geographic locations, or the like. Moreover, the system contemplates the use, sale or distribution of any goods, services or information over any network having similar functionality described herein.

In one exemplary embodiment, each client customer may be issued an "account" or "account number". As used herein, the account or account number may include any device, code, number, letter, symbol, digital certificate, smart chip, digital signal, analog signal, biometric or other identifier/indicia suitably configured to allow the consumer to access, interact with or communicate with the system (e.g., one or more of an authorization/access code, personal identification number (PIN), Internet code, other identification code, and/or the like). The account number may optionally be located on or associated with a charge card, credit card, debit card, prepaid card, embossed card, smart card, magnetic stripe card, bar code card, transponder, radio frequency card or an associated account. The system may include or interface with any of the foregoing cards or devices, or a fob having a transponder and RFID reader in RF communication with the fob. Although the system may include a fob embodiment, the invention is not to be so limited. Indeed, system may include any device having a transponder which is configured to communicate with RFID reader via RF communication. Typical devices may include, for example, a key ring, tag, card, cell phone, wristwatch or any such form capable of being presented for interrogation. Moreover, the system, computing unit or device discussed herein may include a "pervasive computing device," which may include a traditionally non-computerized device that is embedded with a computing unit. The account number may be distributed and stored in any form of plastic, electronic, magnetic, radio frequency, wireless, audio and/or optical device capable of transmitting or downloading data from itself to a second device.

As will be appreciated by one of ordinary skill in the art, the system may be embodied as a customization of an existing system, an add-on product, upgraded software, a stand alone system, a distributed system, a method, a data processing system, a device for data processing, and/or a computer program product. Accordingly, the system may take the form of an entirely software embodiment, an entirely hardware embodiment, or an embodiment combining aspects of both software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

Referring now to FIGS. 2-25 the process flows and screenshots depicted are merely embodiments and are not intended to limit the scope of the invention as described herein. For example, the steps recited in any of the method or process descriptions may be executed in any order and are not limited to the order presented. It will be appreciated that the following description makes appropriate references not only to the steps and user interface elements depicted in FIGS. 2-25, but also to the various system components as described above with reference to FIG. 1.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical".

FIG. 1 is a block diagram of an exemplary embodiment of a system 10 for determining individualized medical intervention for a particular disease state that utilizes molecular profiling of a patient's biological specimen. System 10 includes a user interface 12, a host server 14 including a processor 16 for processing data, a memory 18 coupled to the processor, an application program 20 stored in the memory 18 and accessible by the processor 16 for directing processing of the data by the processor 16, a plurality of internal databases 22 and external databases 24, and an interface with a wired or wireless communications network 26 (such as the Internet, for example). System 10 may also include an input digitizer 28 coupled to the processor 16 for inputting digital data from data that is received from user interface 12.

User interface 12 includes an input device 30 and a display 32 for inputting data into system 10 and for displaying information derived from the data processed by processor 16. User interface 12 may also include a printer 34 for printing the information derived from the data processed by the processor 16 such as patient reports that may include test results for targets and proposed drug therapies based on the test results.

Internal databases 22 may include, but are not limited to, patient biological sample/specimen information and tracking, clinical data, patient data, patient tracking, file management, study protocols, patient test results from molecular profiling, and billing information and tracking. External databases 24 nay include, but are not limited to, drug libraries, gene libraries, disease libraries, and public and private databases such as UniGene, OMIM, GO, TIGR, GenBank, KEGG and Biocarta.

Figure 2:
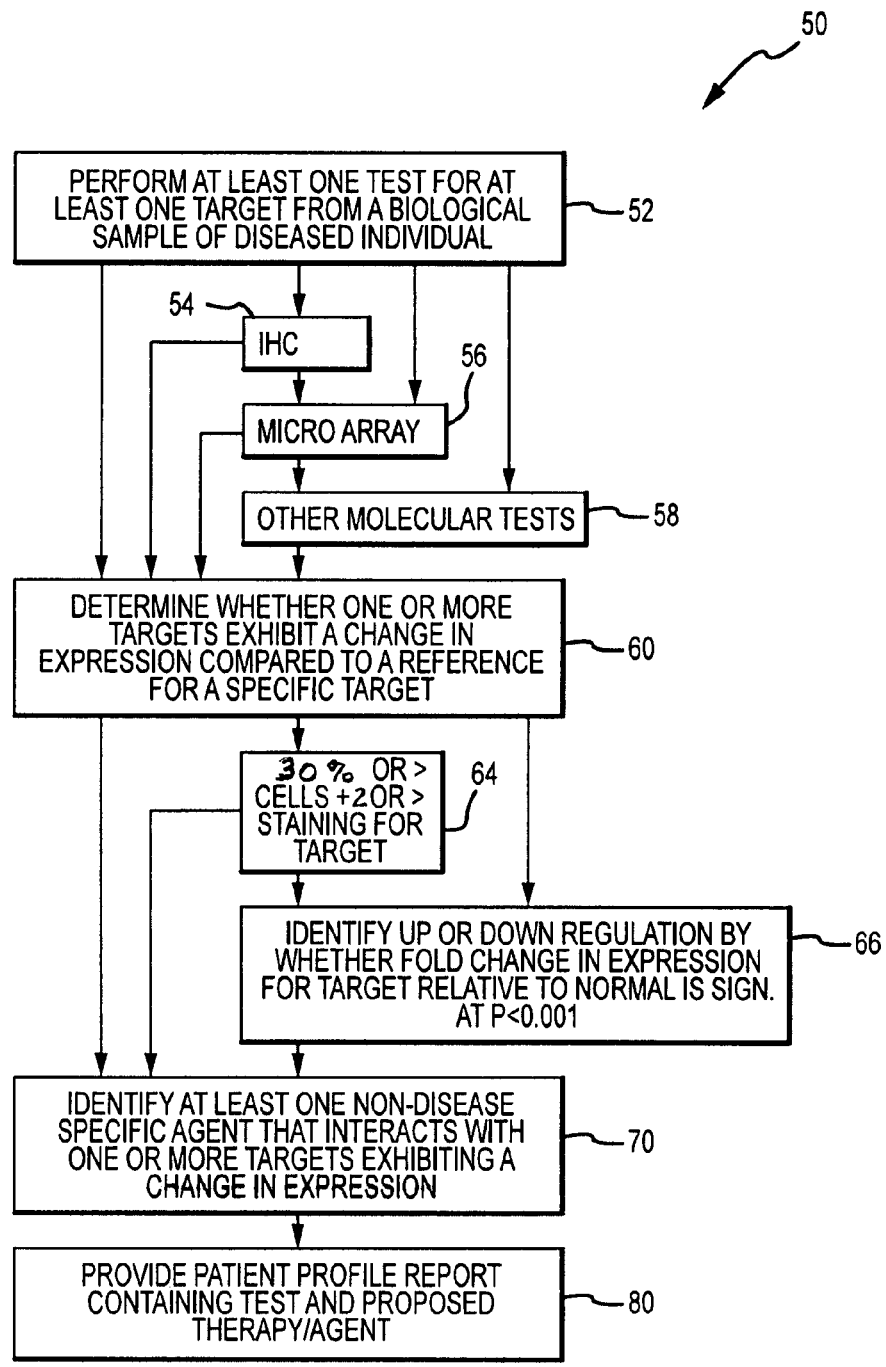
FIG. 2 is a flowchart of an exemplary embodiment of a method for determining individualized medical intervention for a particular disease state that utilizes molecular profiling of a patient's biological specimen that is non disease specific.

Various methods may be used in accordance with system 10. FIG. 2 shows a flowchart of an exemplary embodiment of a method 50 for determining individualized medical intervention for a particular disease state that utilizes molecular profiling of a patient's biological specimen that is non disease specific. In order to determine a medical intervention for a particular disease state using molecular profiling that is independent of disease lineage diagnosis (i.e. not single disease restricted), at least one test is performed for at least one target from a biological sample of a diseased patient in step 52. A target is defined as any molecular finding that may be obtained from molecular testing. For example, a target may include one or more genes, one or more gene expressed proteins, one or more molecular mechanisms, and/or combinations of such. Tests for finding such targets may include, but are not limited to an immunohistochemical (IHC) analysis, a micro array analysis such as a comparative genomic hybridization (CGH) micro array, a single nucleotide polymorphism (SNP) micro array, a fluorescent in-situ hybridization (FISH), an in-situ hybridization (ISH), and a proteomic array, and other molecular tests known to those skilled in the art. Accordingly, one or more of the following may be performed: an IHC analysis in step 54, a microanalysis in step 56, and other molecular tests know to those skilled in the art in step 58.

Biological samples are obtained from diseased patients by taking a biopsy of a tumor, conducting minimally invasive surgery if no recent tumor is available, obtaining a sample of the patient's blood, or a sample of any other biological fluid including, but not limited to, cell extracts, nuclear extracts, cell lysates or biological products or substances of biological origin such as excretions, blood, sera, plasma, urine, sputum, tears, feces, saliva, membrane extracts, and the like.

In step 60, a determination is made as to whether one or more of the targets that were tested for in step 52 exhibit a change in expression compared to a normal reference for that particular target. In one exemplary method of the invention, an IHC analysis may be performed in step 54 and a determination as to whether any targets from the IHC analysis exhibit a change in expression is made in step 64 by determining whether 30% or more of the biological sample cells were +2 or greater staining for the particular target. It will be understood by those skilled in the art that there will be instances where +1 or greater staining will indicate a change in expression in that staining results may vary depending on the technician performing the test and type of target being tested. In another exemplary embodiment of the invention, a micro array analysis may be performed in step 56 and a determination as to whether any targets from the micro array analysis exhibit a change in expression is made in step 66 by identifying which targets are up-regulated or down-regulated by determining whether the fold change in expression for a particular target relative to a normal tissue of origin reference is significant at $p<0.001$. A change in expression may also be evidenced by an absence of one or more genes, gene expressed proteins, molecular mechanisms, or other molecular findings.

After determining which targets exhibit a change in expression in step 60, at least one non-disease specific agent is identified that interacts with each target having a changed expression in step 70. An agent may be any drug or compound having a therapeutic effect. A non-disease specific agent is a therapeutic drug or compound not previously associated with treating the patient's diagnosed disease that is capable of interacting with the target from the patient's biological sample that has exhibited a change in expression. Some of the non-disease specific agents that have been found to interact with specific targets found in different cancer patients are shown in Table 1 below.

TABLE 1

| Patients | Target(s) Found | Treatment(s) |
|---|---|---|
| Advanced Pancreatic Cancer | HER 2/neu (IHC/Array) | Herceptin ™ |
| Advanced Pancreatic Cancer | EGFR (IHC), HIF 1α | Erbitux ™, Rapamycin ™ |
| Advanced Ovarian Cancer | ERCC3 (Array) | Irofulvene |
| Advanced Adenoid Cystic Carcinoma | Vitamin D receptors, Androgen receptors | Calcitriol ™, Flutamide ™ |

Finally, in step 80, a patient profile report may be provided which includes the patient's test results for various targets and any proposed therapies based on those results. An exemplary patient profile report 100 is shown in FIGS. 3A-3D. Patient profile report 100 shown in FIG. 3A identifies the targets tested 102, those targets tested that exhibited significant changes in expression 104, and proposed non-disease specific agents for interacting with the targets 106. Patient profile report 100 shown in FIG. 3B identifies the results 108 of immunohistochemical analysis for certain gene expressed proteins 110 and whether a gene expressed protein is a molecular target 112 by determining whether 30% or more of the tumor cells were +2 or greater staining. Report 100 also identifies immunohistochemical tests that were not performed 114. Patient profile report 100 shown in FIG. 3C identifies the genes analyzed 116 with a micro array analysis and whether the genes were under expressed or over expressed 118 compared to a reference. Finally, patient profile report 100 shown in FIG. 3D identifies the clinical history 120 of the patient and the specimens that were submitted 122 from the patient.

Figure 4:
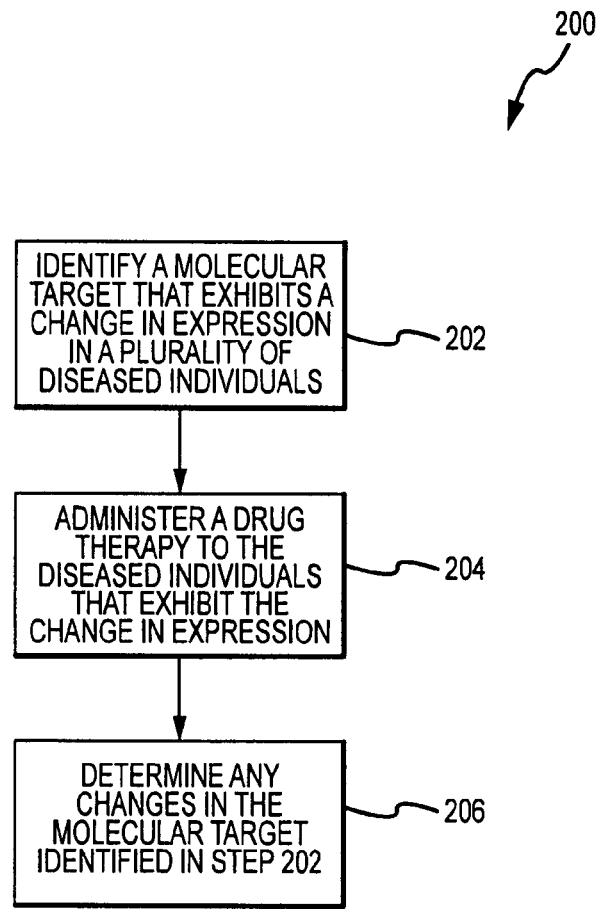
FIG. 4 is a flowchart of an exemplary embodiment of a method for identifying a drug therapy/agent capable of interacting with a target.

FIG. 4 shows a flowchart of an exemplary embodiment of a method 200 for identifying a drug therapy/agent capable of interacting with a target. In step 202, a molecular target is identified which exhibits a change in expression in a number of diseased individuals. Next, in step 204, a drug therapy/agent is administered to the diseased individuals. After drug therapy/agent administration, any changes in the molecular target identified in step 202 are identified in step 206 in order to determine if the drug therapy/agent administered in step 204 interacts with the molecular targets identified in step 202. If it is determined that the drug therapy/agent administered in step 204 interacts with a molecular target identified in step 202, the drug therapy/agent may be approved for treating patients exhibiting a change in expression of the identified molecular target instead of approving the drug therapy/agent for a particular disease.

Figure 5:
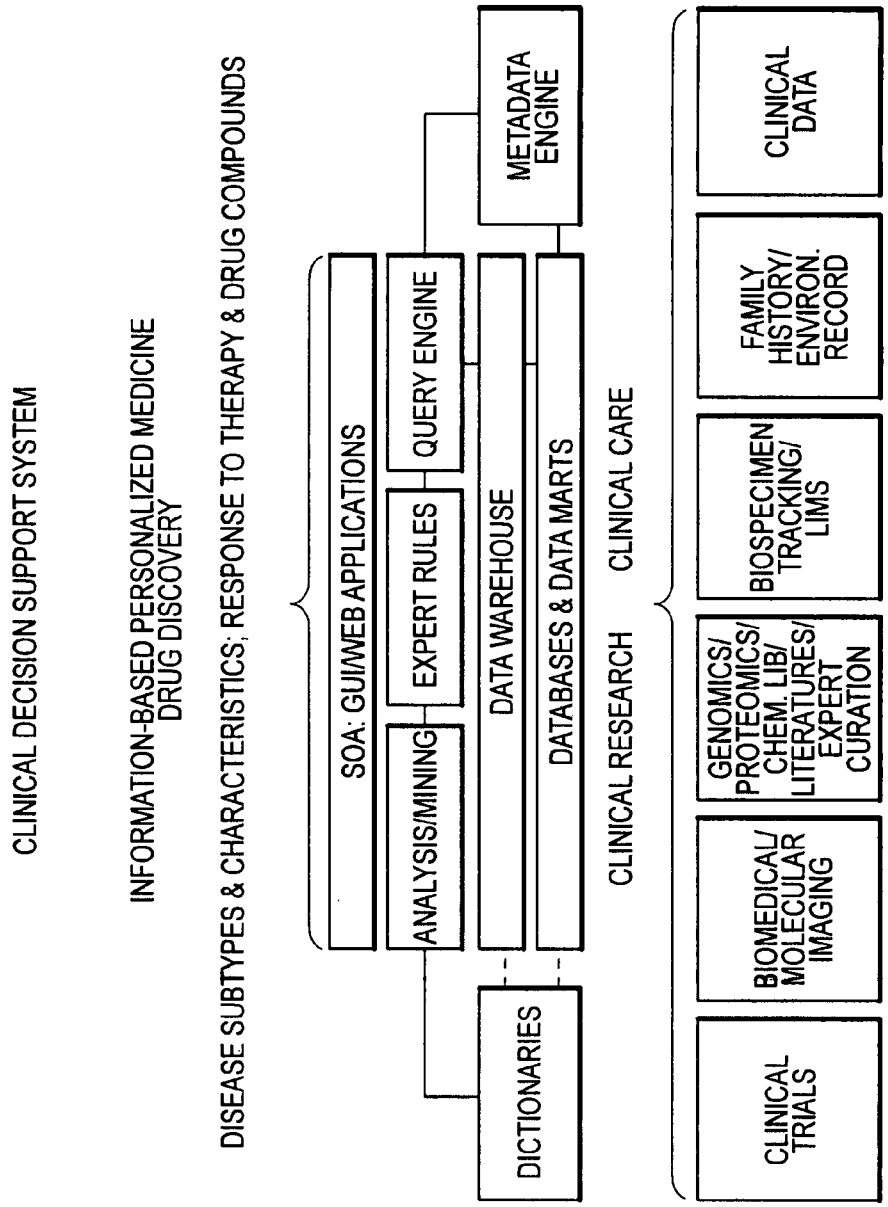
FIGS. 5-14 are flowcharts and diagrams illustrating various parts of an information-based personalized medicine drug discovery system and method in accordance with the present invention.
Figure 6:
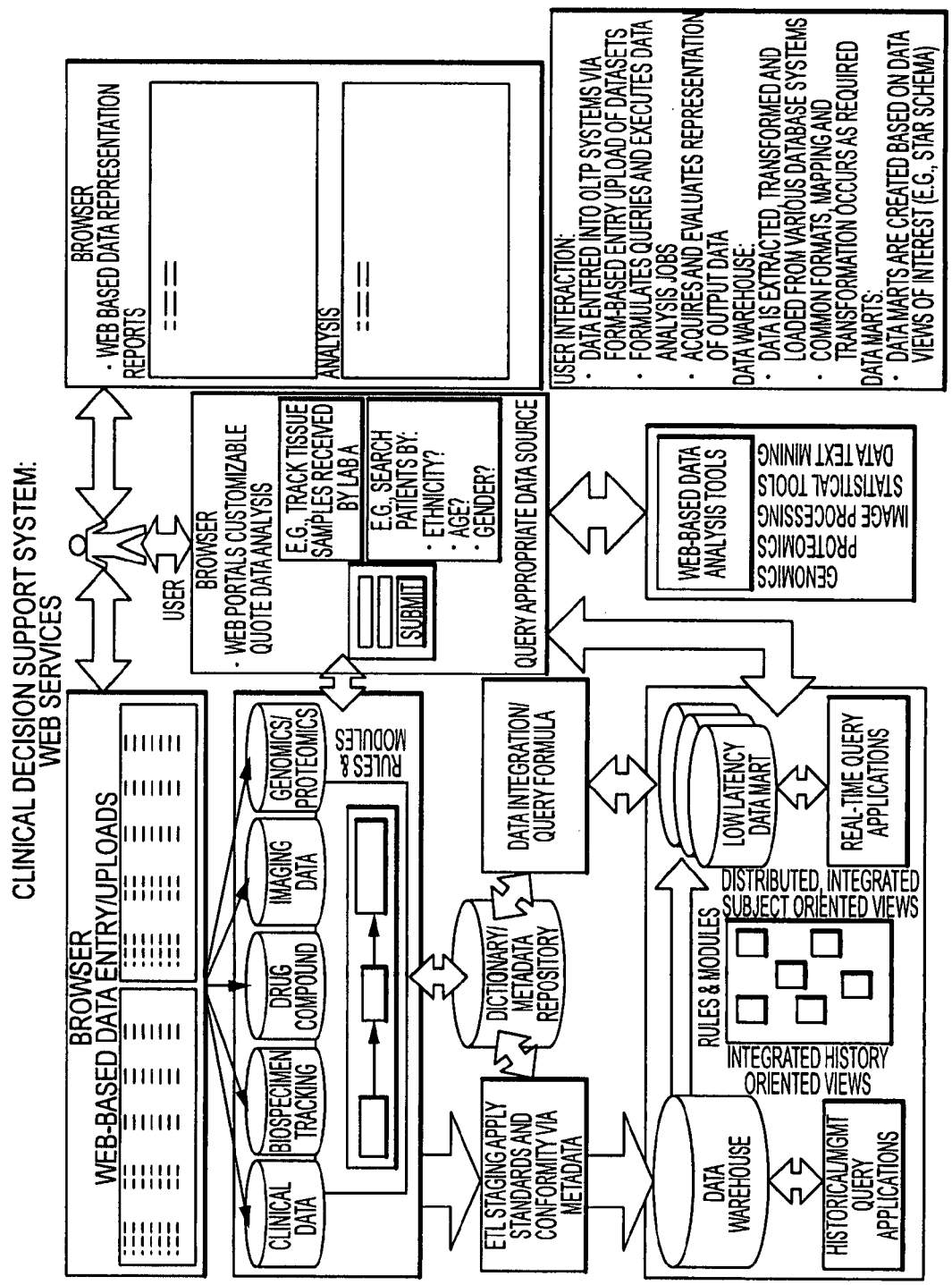

FIGS. 5-14 are flowcharts and diagrams illustrating various parts of an information-based personalized medicine drug discovery system and method in accordance with the present invention. FIG. 5 is a diagram showing an exemplary clinical decision support system of the information-based personalized medicine drug discovery system and method of the present invention. Data obtained through clinical research and clinical care such as clinical trial data, biomedical/molecular imaging data, genomics/proteomics/chemical library/literature/expert curation, biospecimen tracking/LIMS, family history/environmental records, and clinical data are collected and stored as databases and datamarts within a data warehouse. FIG. 6 is a diagram showing the flow of information through the clinical decision support system of the information-based personalized medicine drug discovery system and method of the present invention using web services. A user interacts with the system by entering data into the system via form-based entry/upload of data sets, formulating queries and executing data analysis jobs, and acquiring and evaluating representations of output data. The data warehouse in the web based system is where data is extracted, transformed, and loaded from various database systems. The data warehouse is also where common formats, mapping and transformation occurs. The web based system also includes datamarts which are created based on data views of interest.

Figure 7:
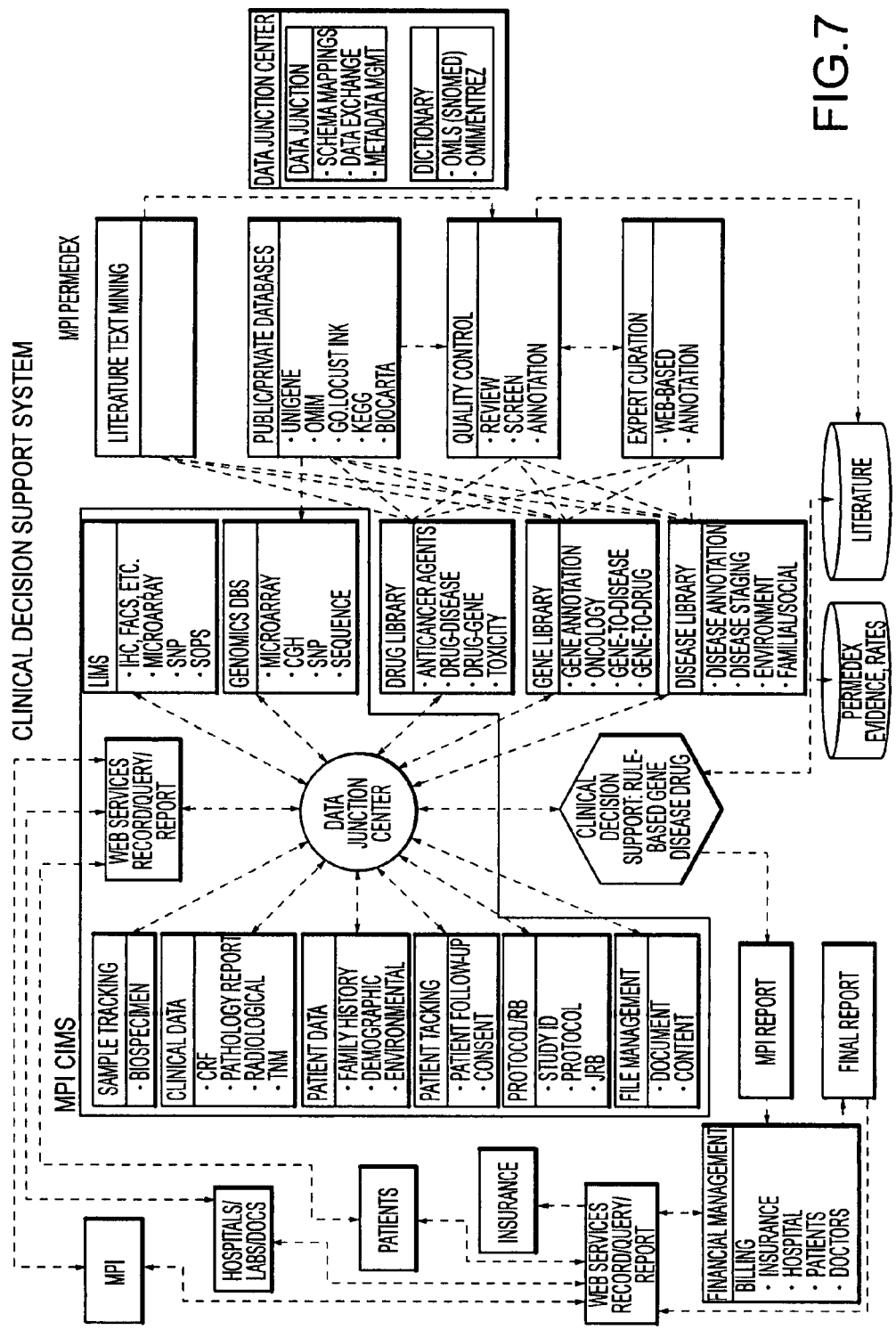

A flow chart of an exemplary clinical decision support system of the information-based personalized medicine drug discovery system and method of the present invention is shown in FIG. 7. The clinical information management system includes the laboratory information management system and the medical information contained in the data warehouses and databases includes medical information libraries, such as drug libraries, gene libraries, and disease libraries, in addition to literature text mining. Both the information management systems relating to particular patients and the medical information databases and data warehouses come together at a data junction center where diagnostic information and therapeutic options can be obtained. A financial management system may also be incorporated in the clinical decision support system of the information-based personalized medicine drug discovery system and method of the present invention.

Figure 8:
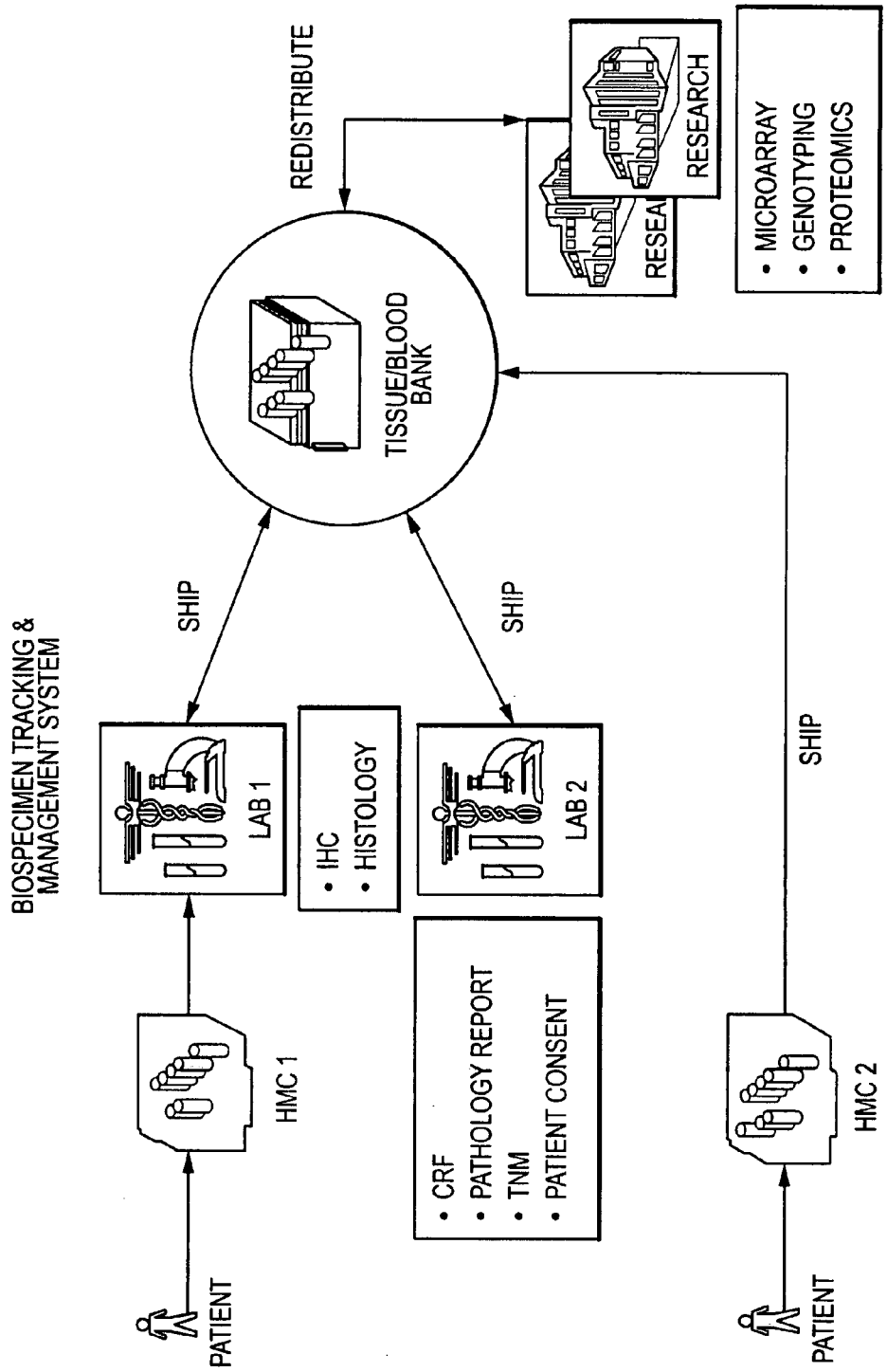
Figure 9:
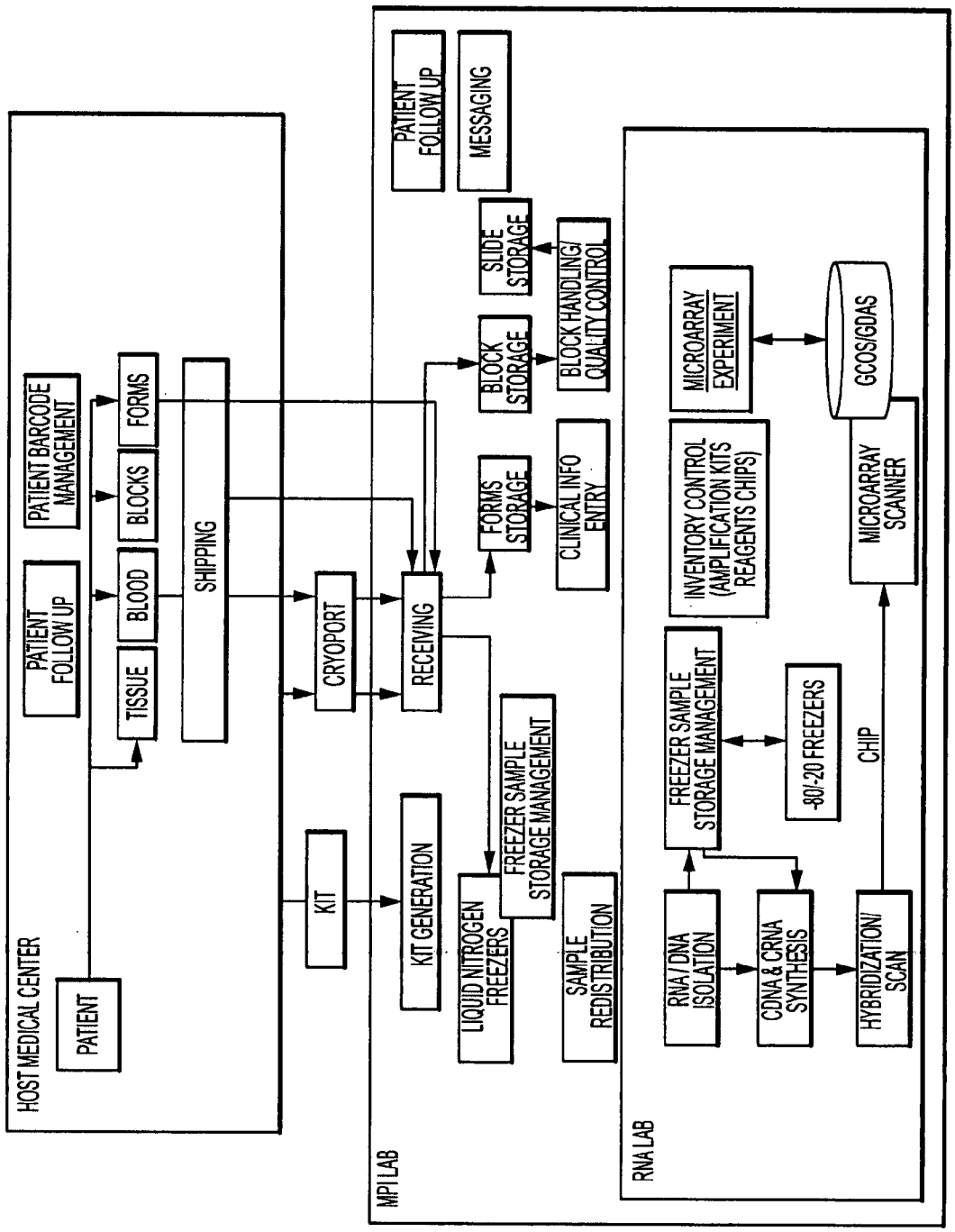

FIG. 8 is a diagram showing an exemplary biospecimen tracking and management system which may be utilized as part of the information-based personalized medicine drug discovery system and method of the present invention. FIG. 8 shows two host medical centers which forward specimens to a tissue/blood bank. The specimens may go through laboratory analysis prior to shipment. Research may also be conducted on the samples via micro array, genotyping, and proteomic analysis. This information can be redistributed to the tissue/blood bank. FIG. 9 depicts a flow chart of an exemplary biospecimen tracking and management system which may be utilized with the information-based personalized medicine drug discovery system and method of the present invention. The host medical center obtains samples from patients and then ships the patient samples to a molecular profiling laboratory which may also perform RNA and DNA isolation and analysis.

Figure 10:
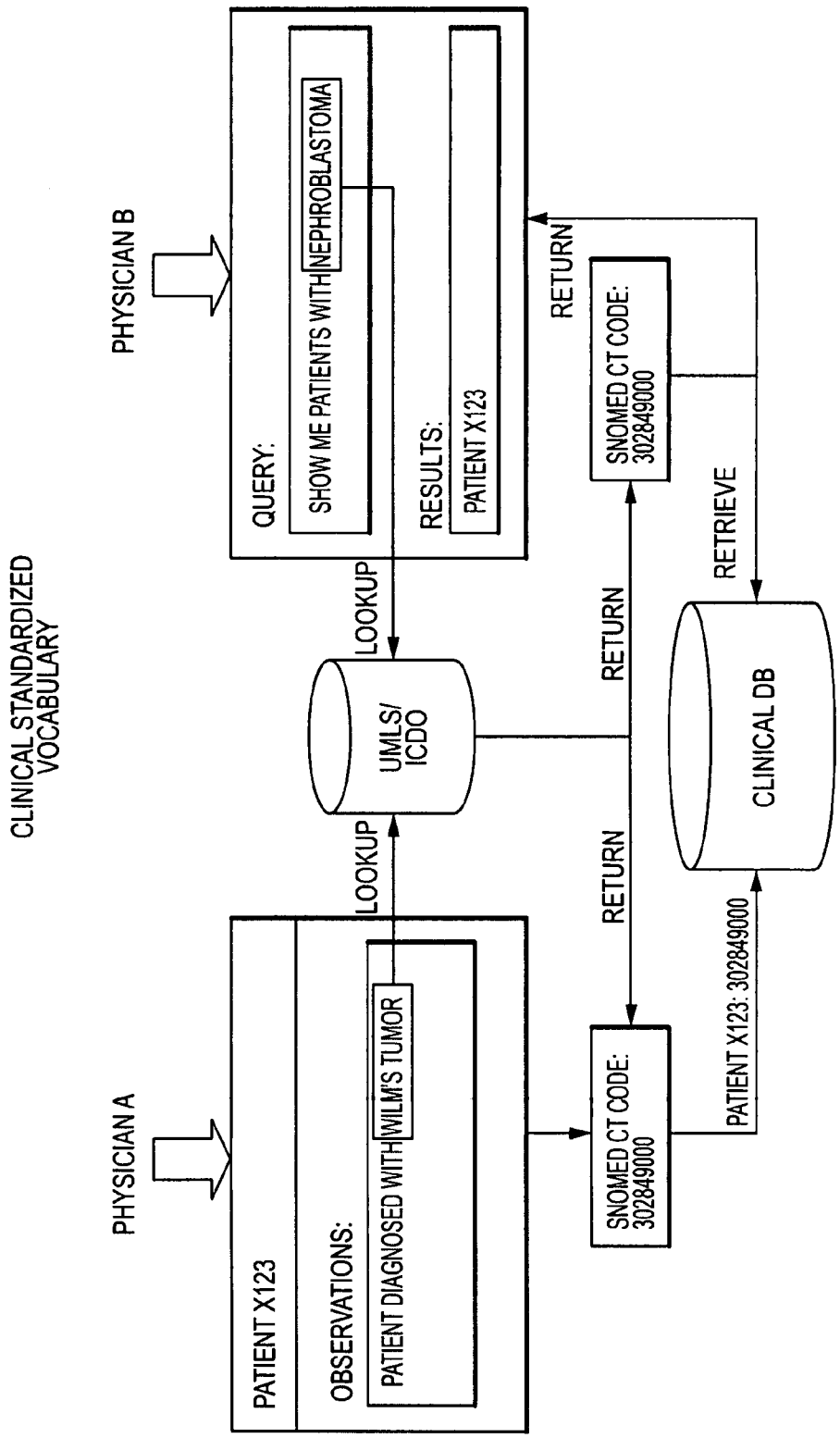

A diagram showing a method for maintaining a clinical standardized vocabulary for use with the information-based personalized medicine drug discovery system and method of the present invention is shown in FIG. 10. FIG. 10 illustrates how physician observations and patient information associated with one physician's patient may be made accessible to another physician to enable the other physician to utilize the data in making diagnostic and therapeutic decisions for their patients.

Figure 11:
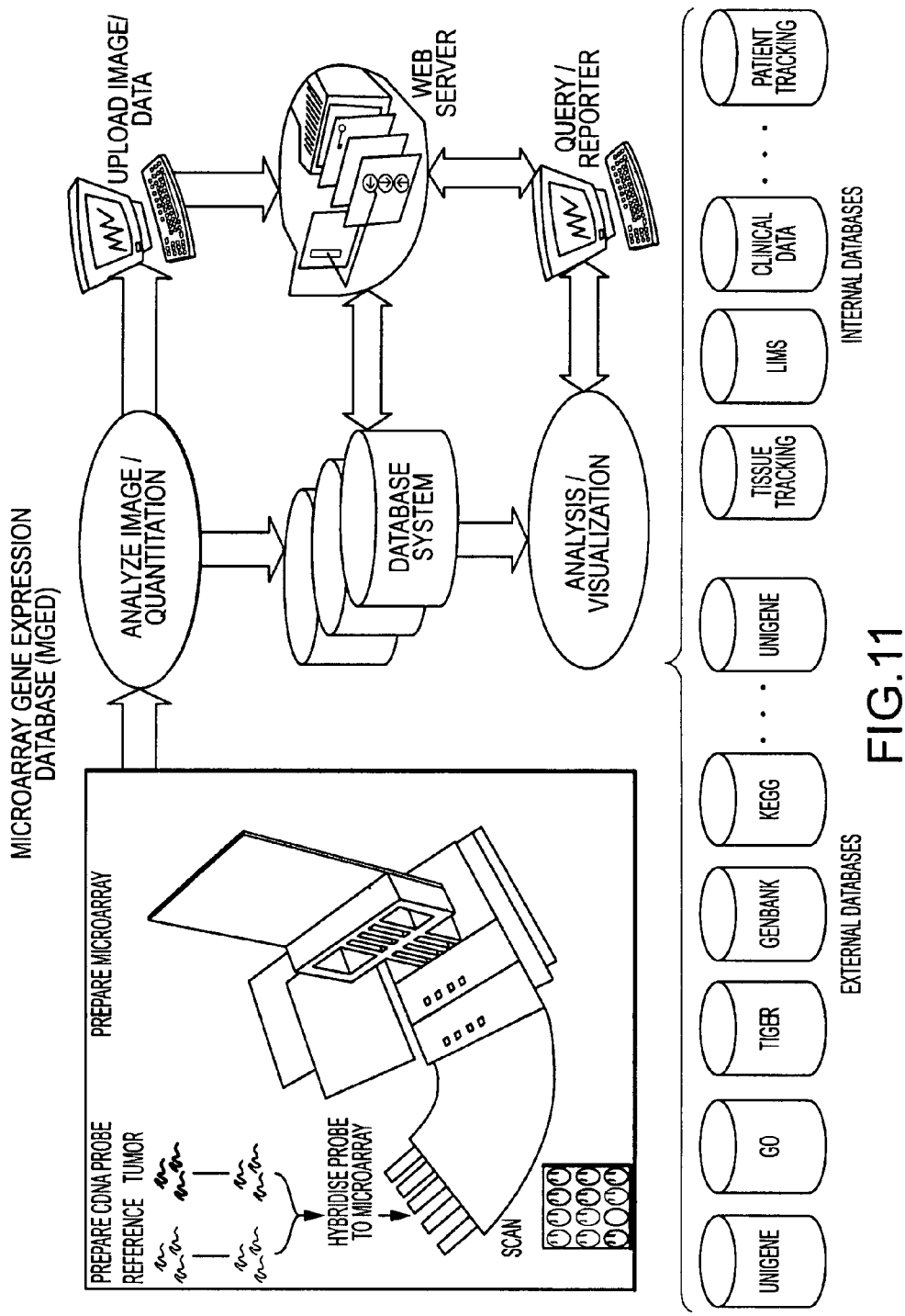
Figure 12:
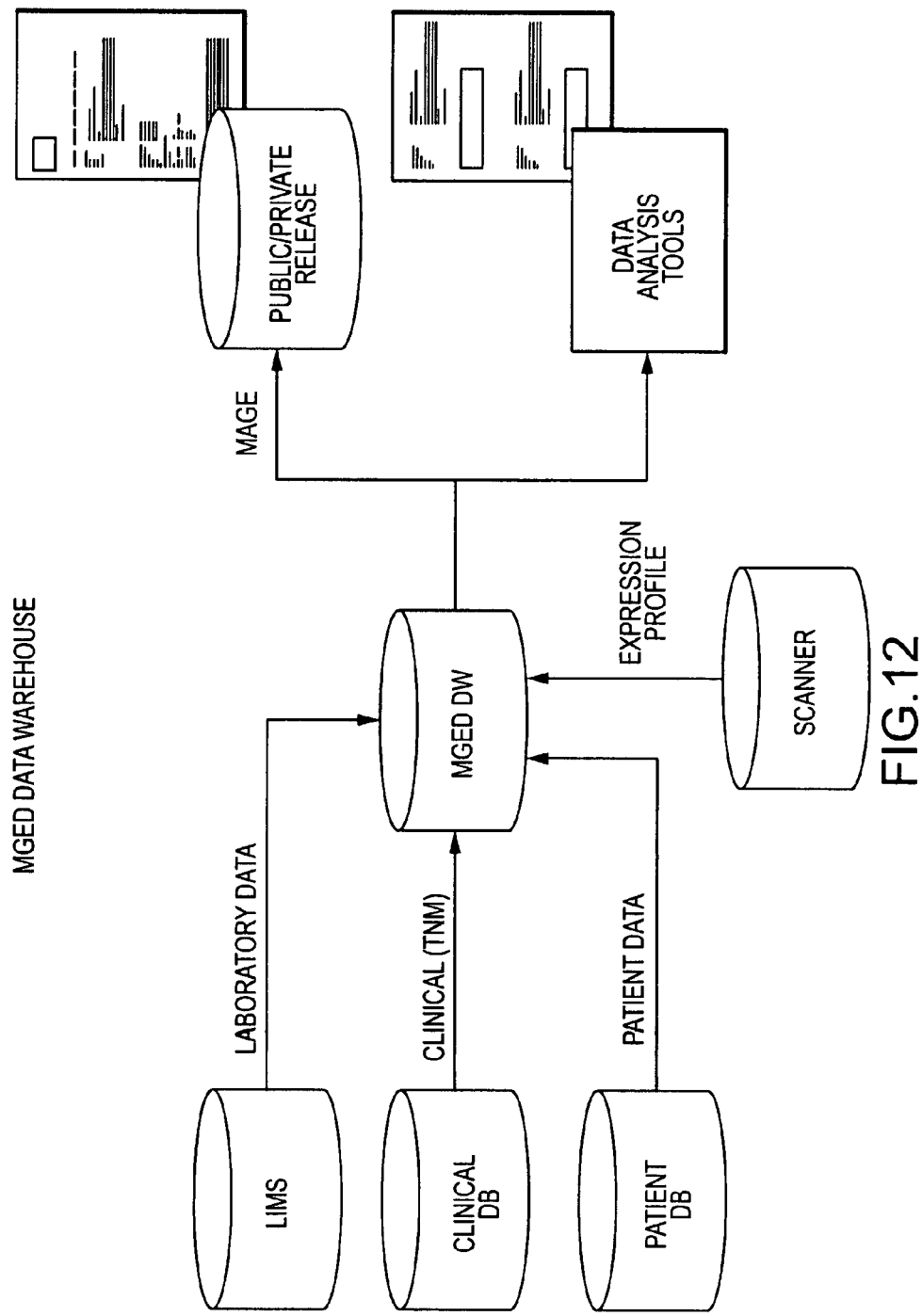

FIG. 11 shows a schematic of an exemplary micro array gene expression database which may be used as part of the information-based personalized medicine drug discovery system and method of the present invention. The micro array gene expression database includes both external databases and internal databases which can be accessed via the web based system. External databases may include, but are not limited to, UniGene, GO, TIGR, GenBank, KEGG. The internal databases may include, but are not limited to, tissue tracking, LIMS, clinical data, and patient tracking. FIG. 12 shows a diagram of an exemplary micro array gene expression database data warehouse which may be used as part of the information-based personalized medicine drug discovery system and method of the present invention. Laboratory data, clinical data, and patient data may all be housed in the micro array gene expression database data warehouse and the data may in turn be accessed by public/private release and utilized by data analysis tools.

Figure 13:
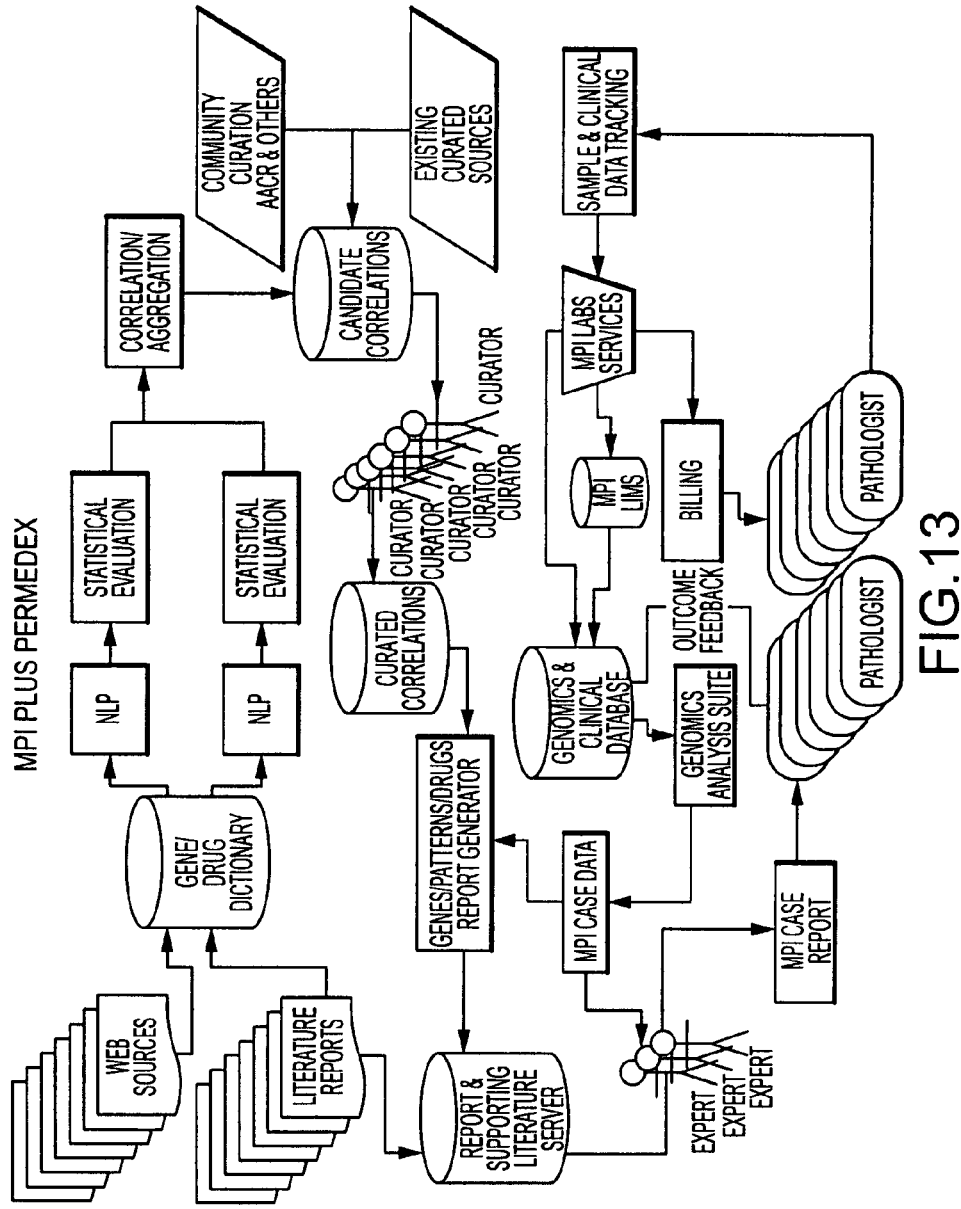
Figure 14:
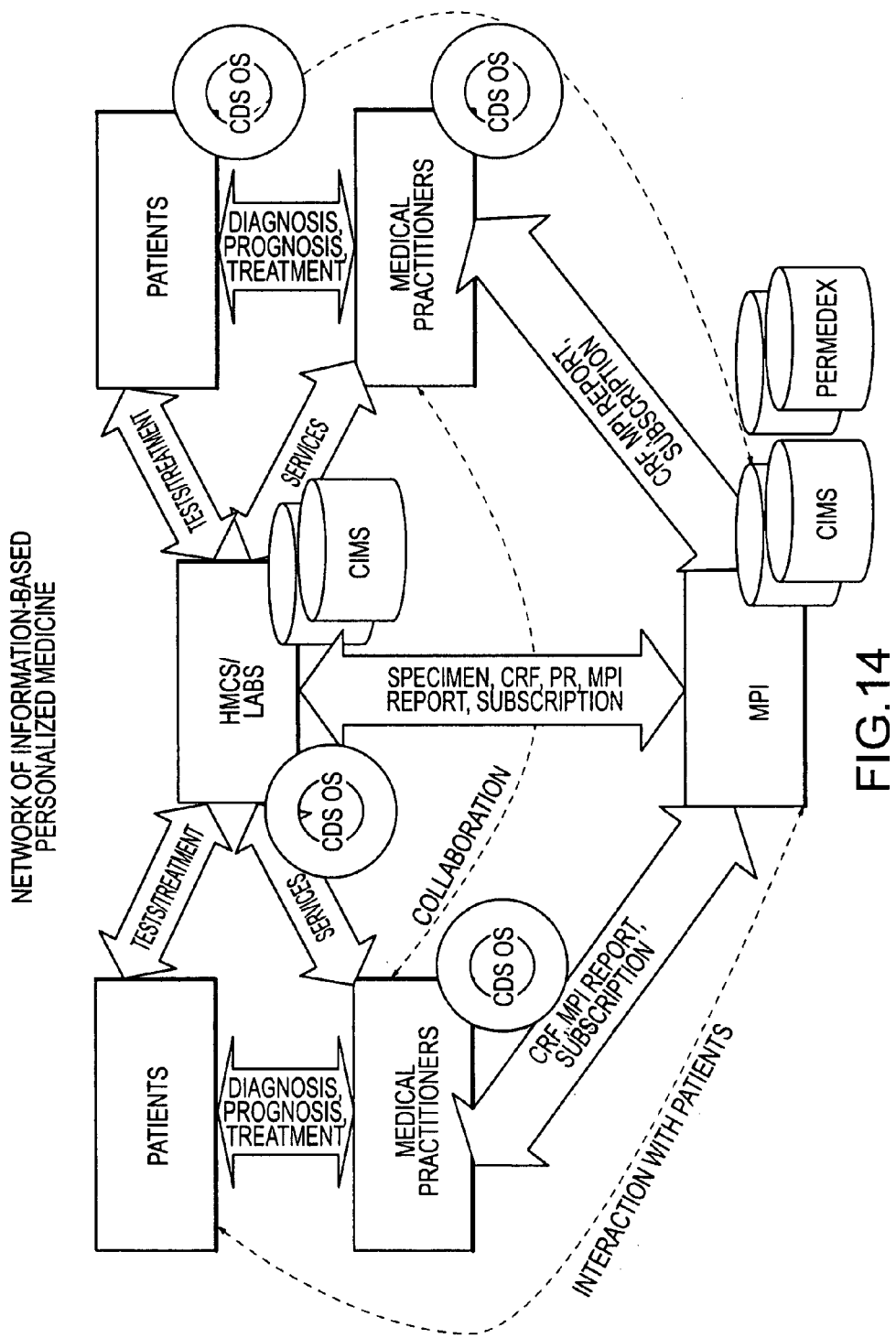

Another schematic showing the flow of information through an information-based personalized medicine drug discovery system and method of the present invention is shown in FIG. 13. Like FIG. 7, the schematic includes clinical information management, medical and literature information management, and financial management of the information-based personalized medicine drug discovery system and method of the present invention. FIG. 14 is a schematic showing an exemplary network of the information-based personalized medicine drug discovery system and method of the present invention. Patients, medical practitioners, host medical centers, and labs all share and exchange a variety of information in order to provide a patient with a proposed therapy or agent based on various identified targets.

Figure 16:
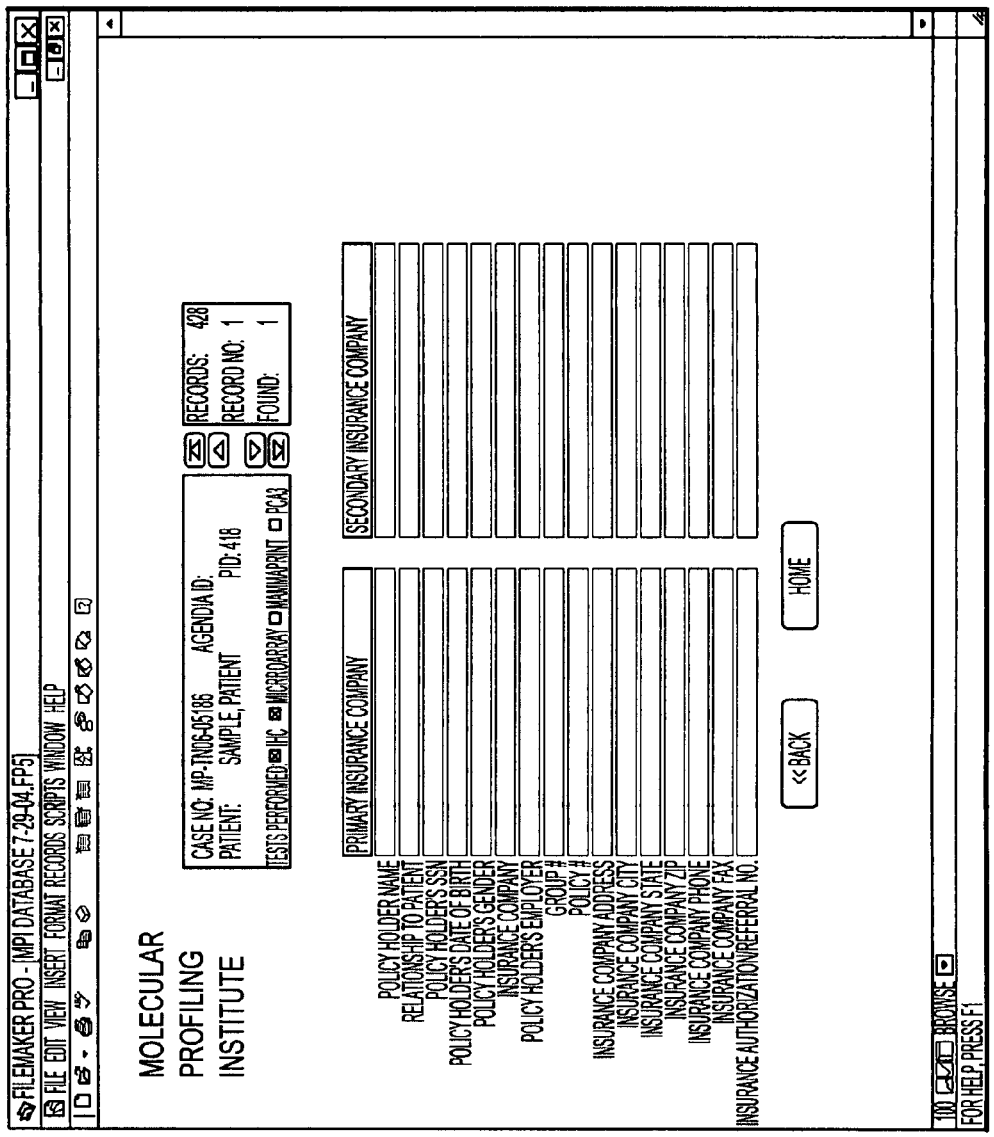
Figure 17:
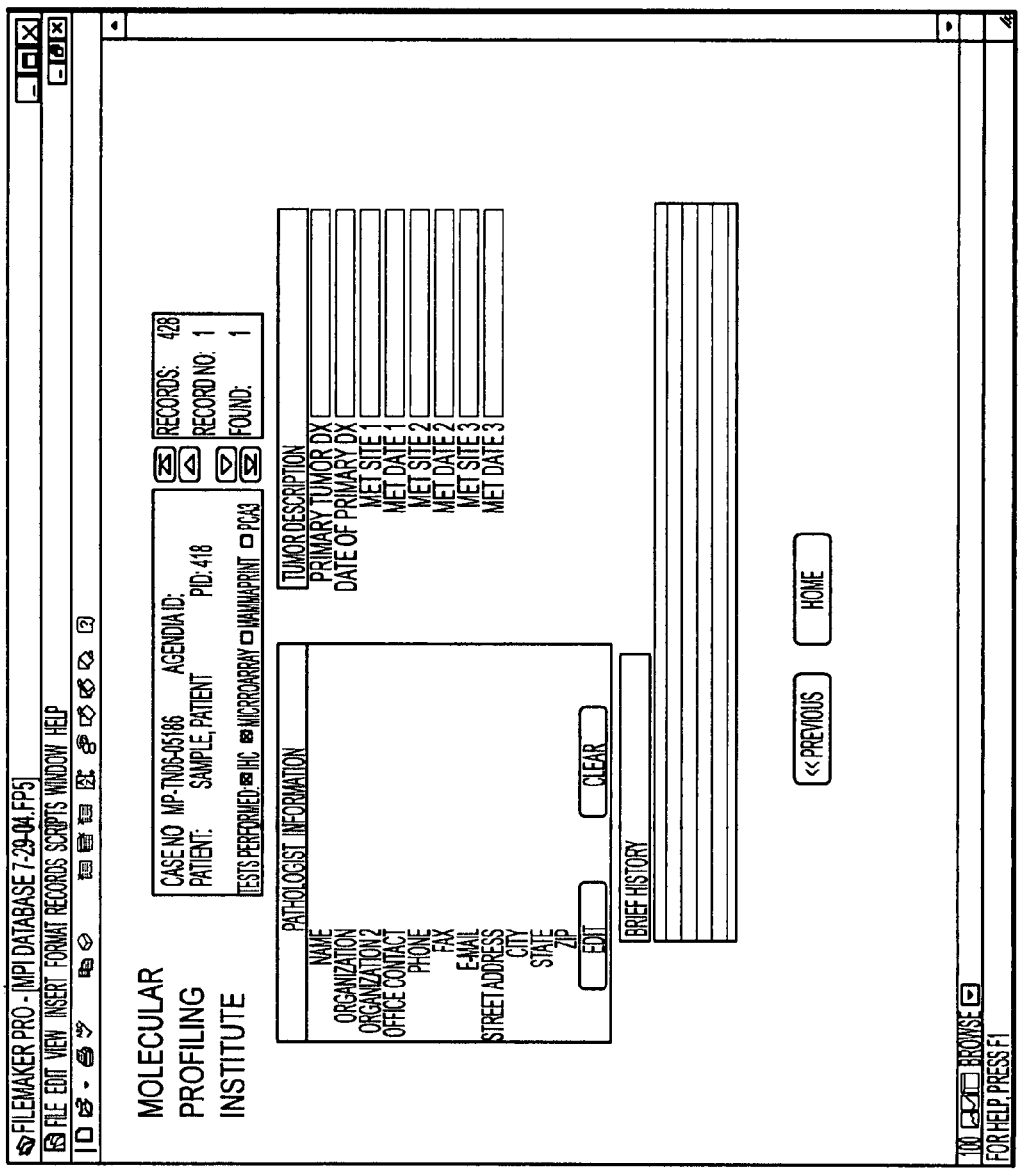
Figure 19:
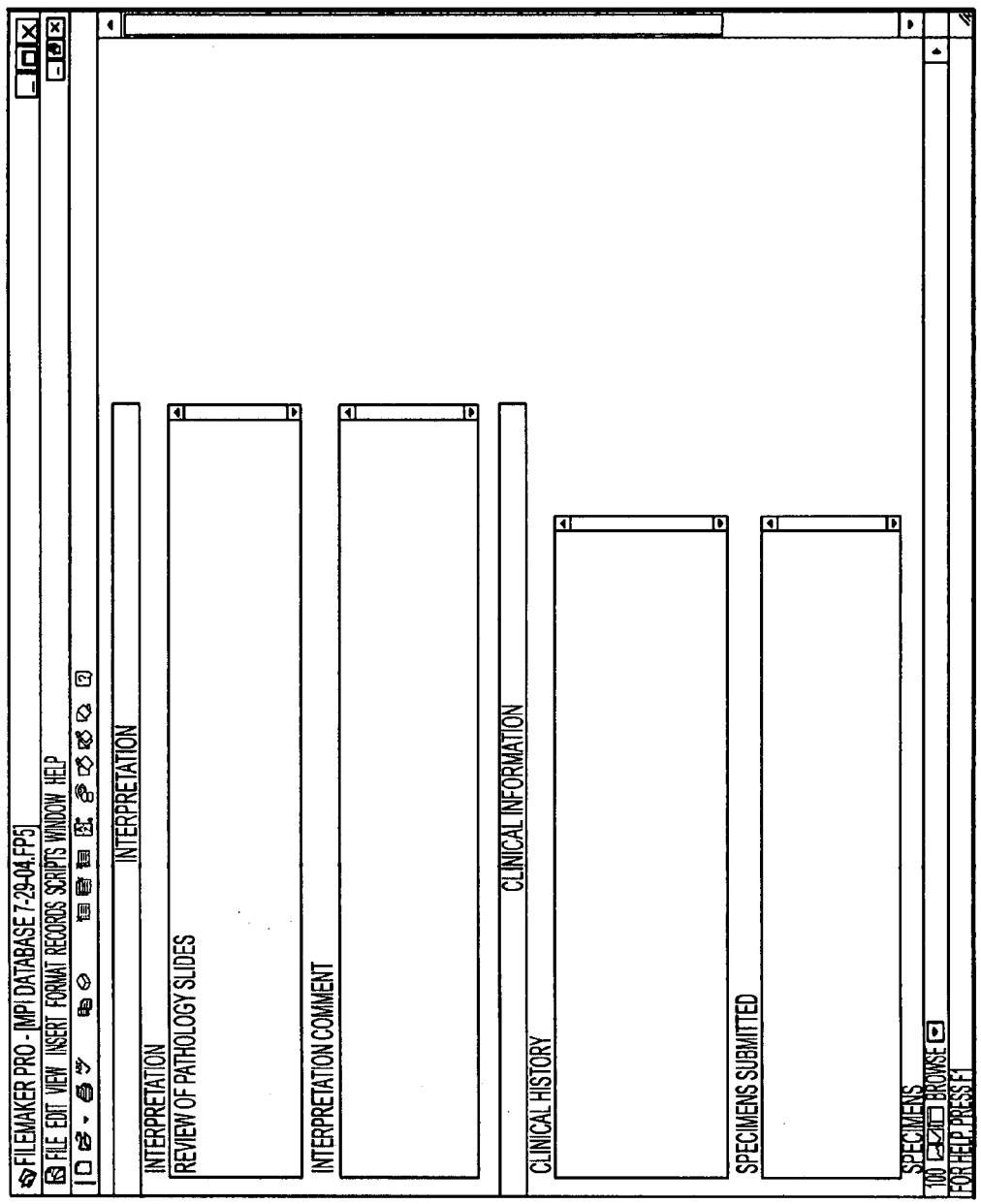

FIGS. 15-25 are computer screen print outs associated with various parts of the information-based personalized medicine drug discovery system and method shown in FIGS. 5-14. FIGS. 15 and 16 show computer screens where physician information and insurance company information is entered on behalf of a client. FIGS. 17-19 show computer screens in which information can be entered for ordering analysis and tests on patient samples.

Figure 20:
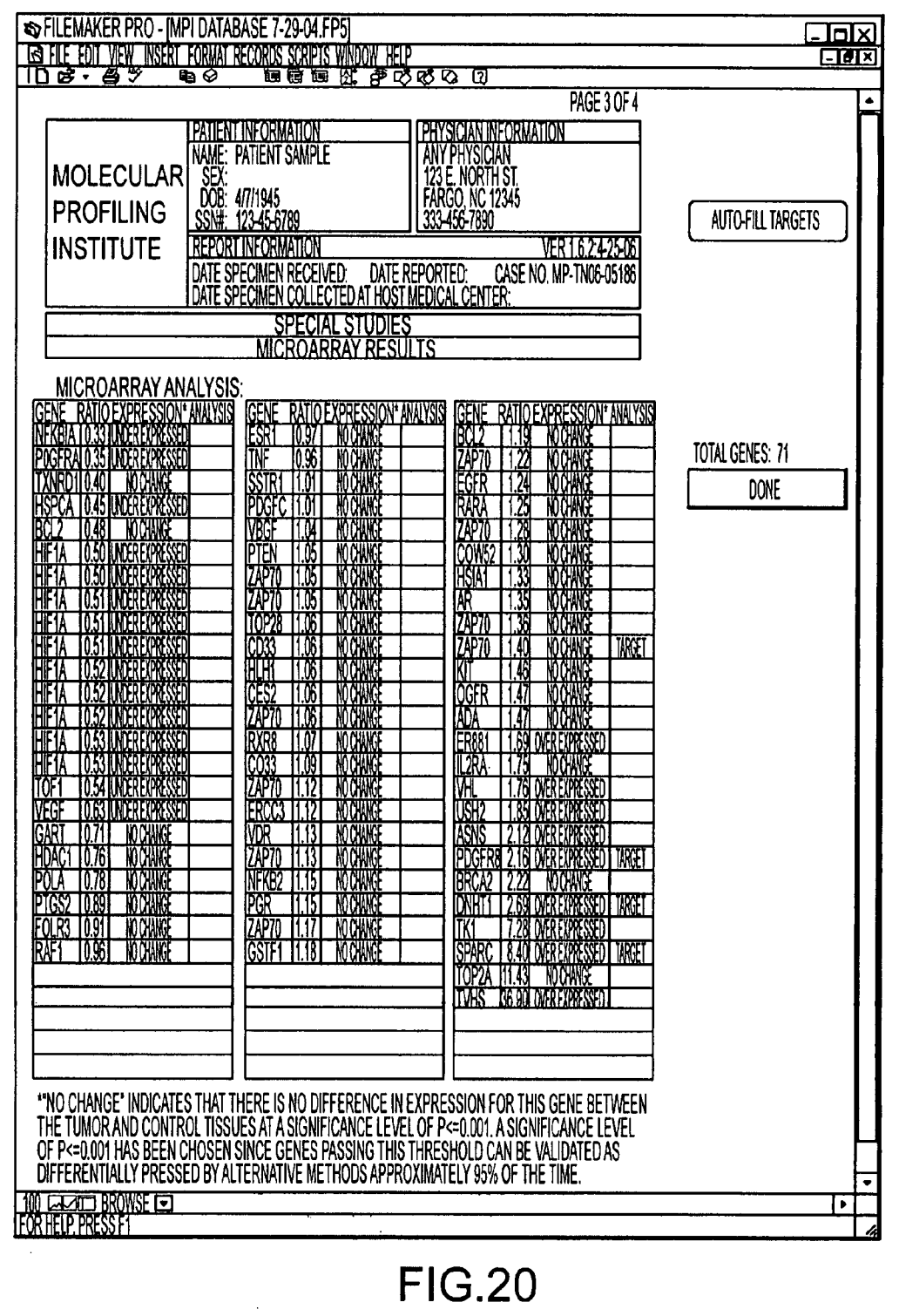
Figure 22:
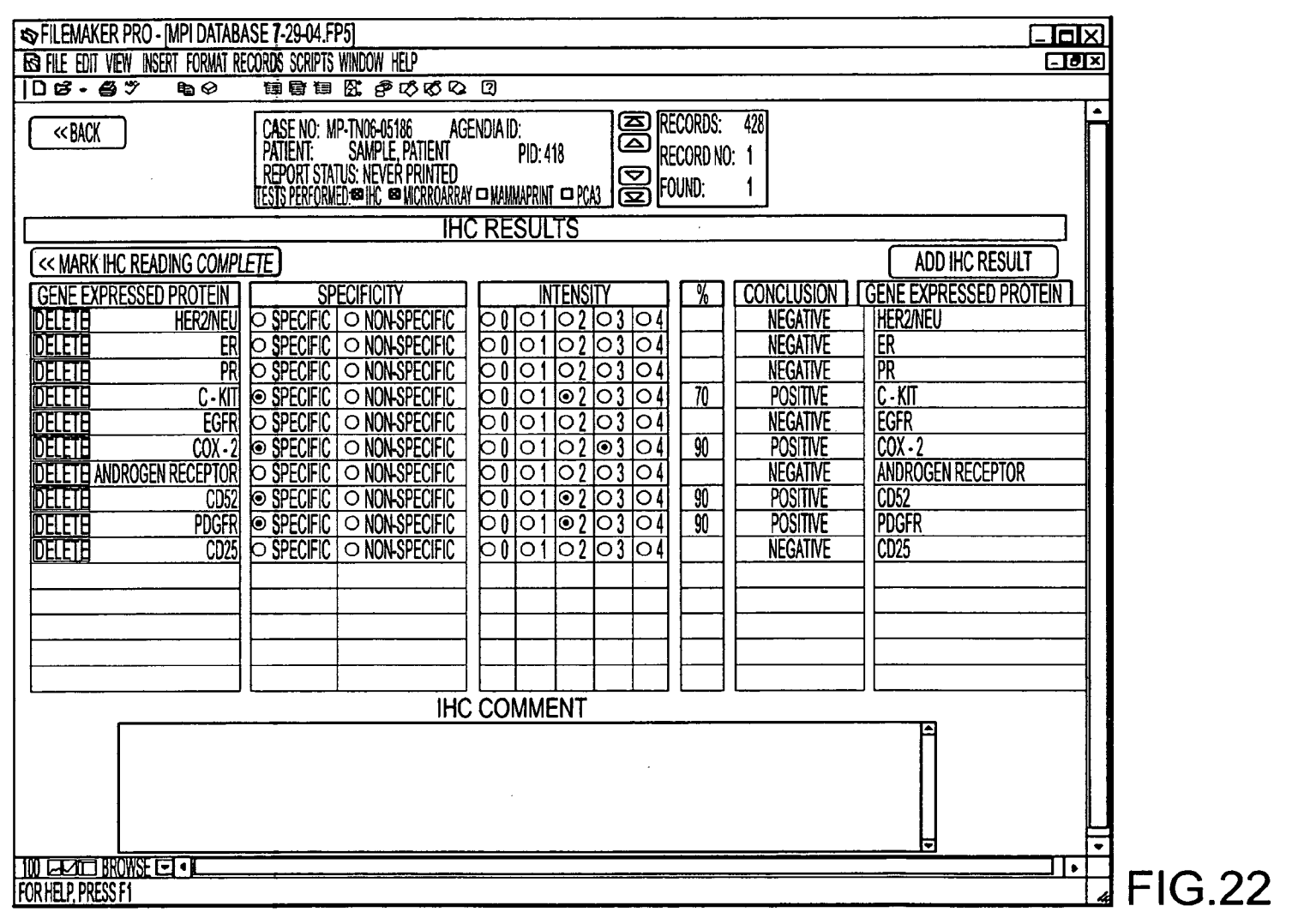

FIG. 20 is a computer screen showing micro array analysis results of specific genes tested with patient samples. This information and computer screen is similar to the information detailed in the patient profile report shown in FIG. 3C. FIG. 22 is a computer screen that shows immunohistochemistry test results for a particular patient for various genes. This information is similar to the information contained in the patient profile report shown in FIG. 3B.

Figure 21:
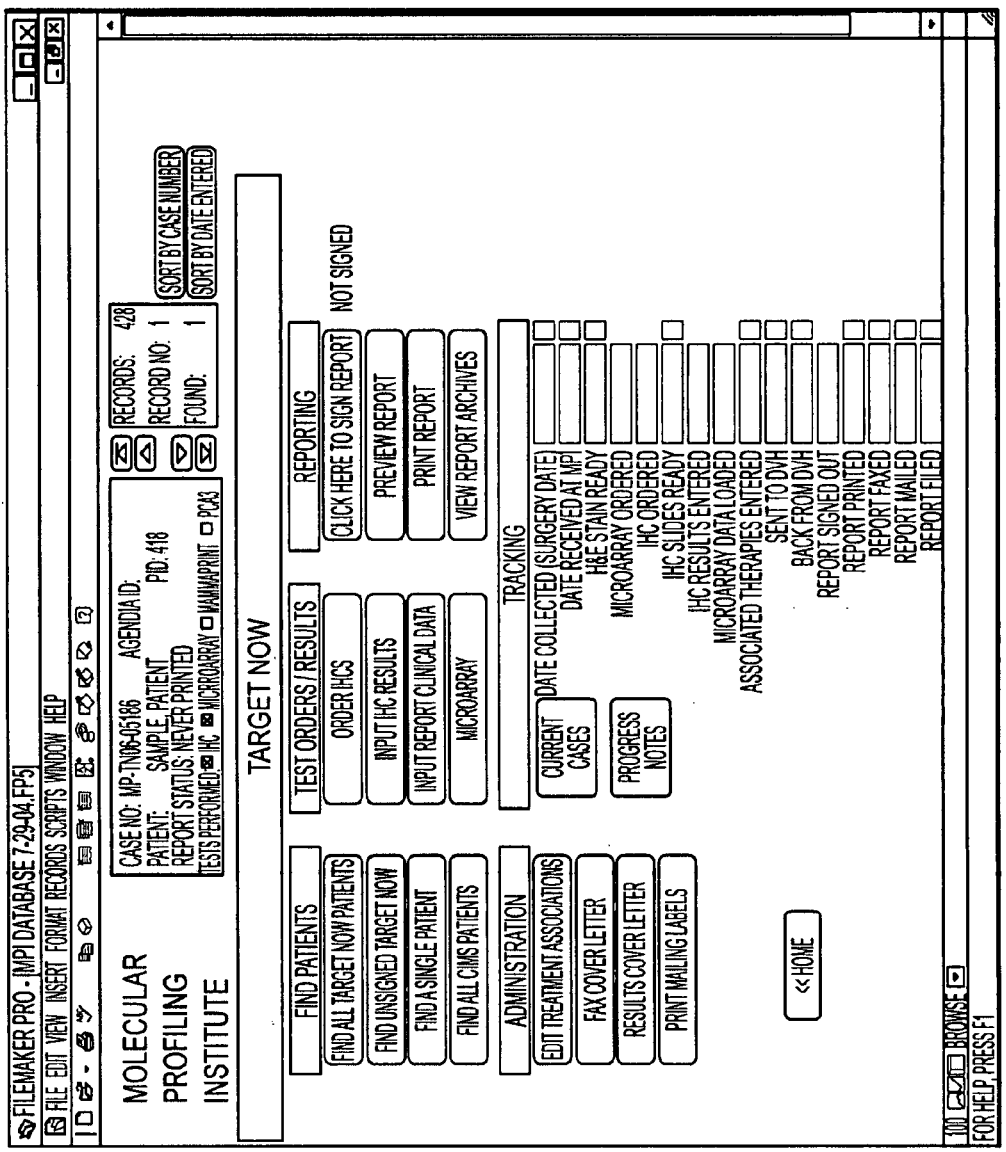

FIG. 21 is a computer screen showing selection options for finding particular patients, ordering tests and/or results, issuing patient reports, and tracking current cases/patients.

Figure 23:
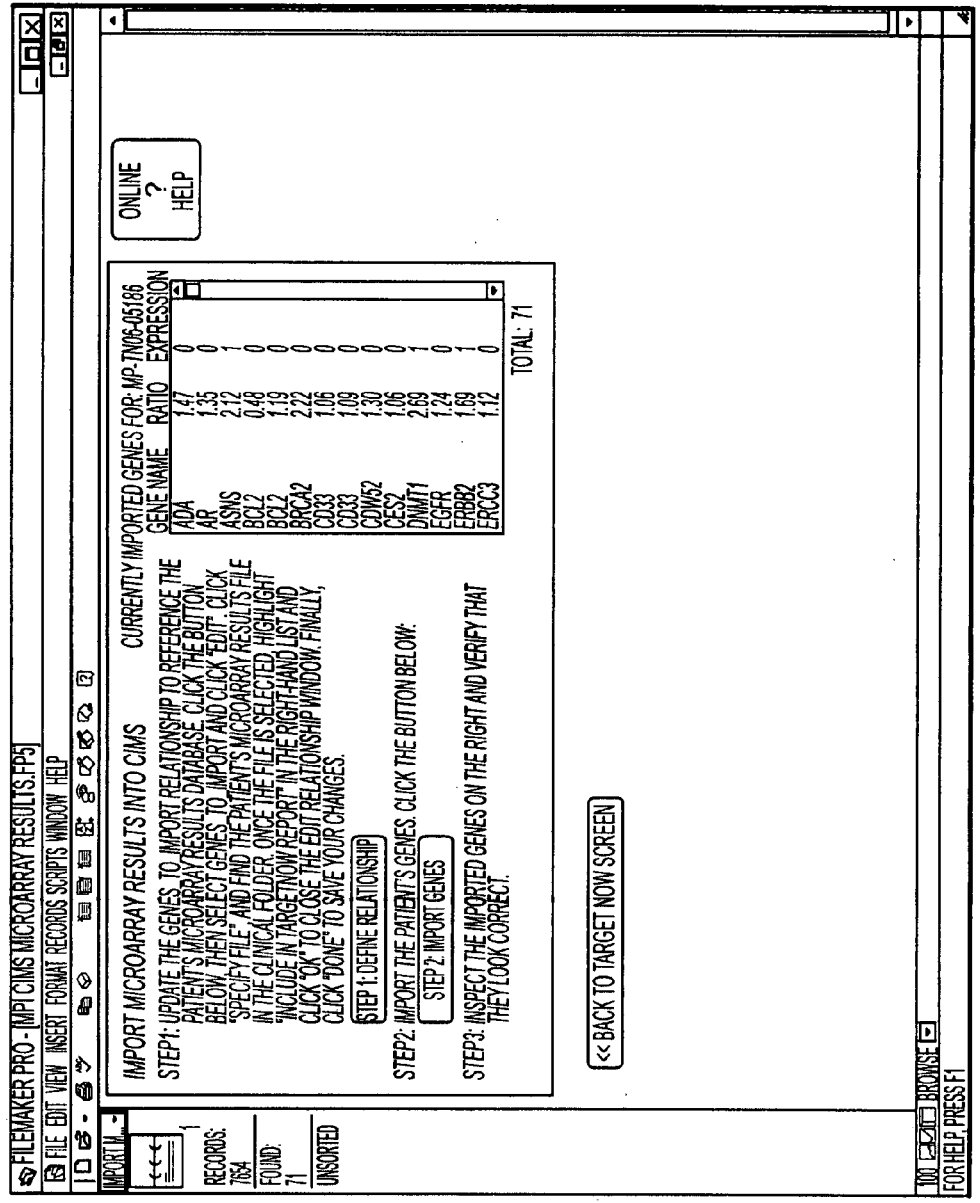
Figure 24:
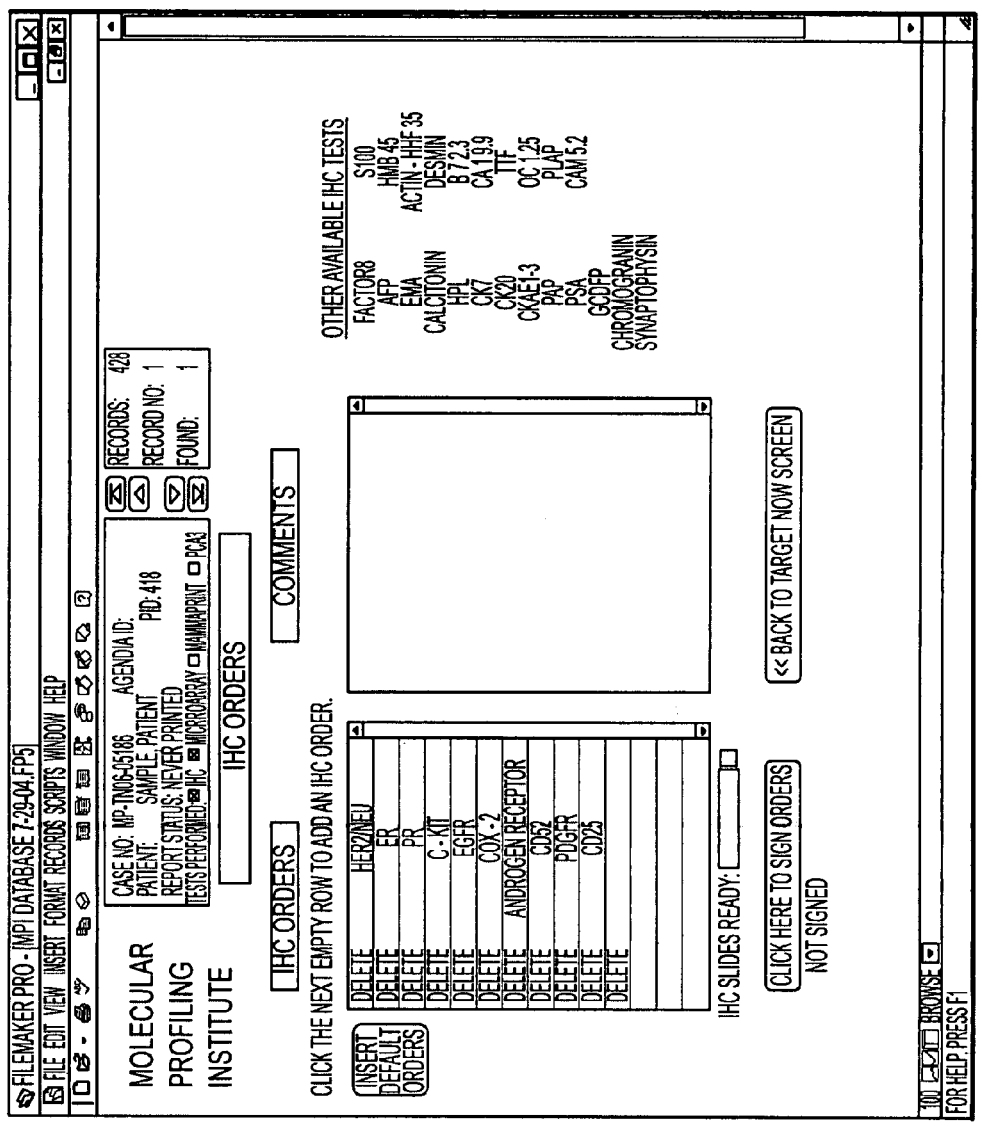
Figure 25:
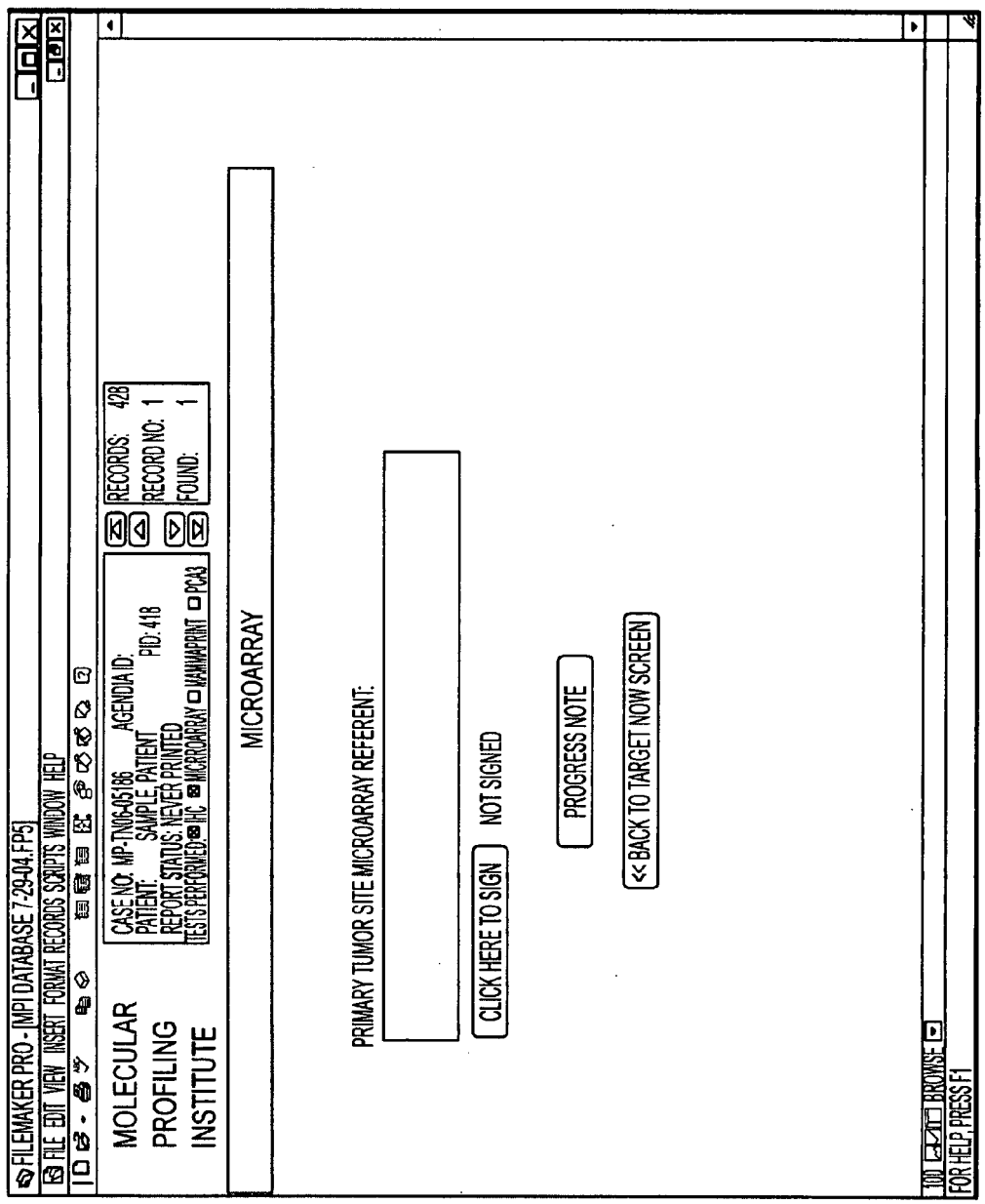

FIG. 23 is a computer screen which outlines some of the steps for creating a patient profile report as shown in FIGS. 3A through 3D. FIG. 24 shows a computer screen for ordering an immunohistochemistry test on a patient sample and FIG. 25 shows a computer screen for entering information regarding a primary tumor site for micro array analysis. It will be understood by those skilled in the art that any number and variety of computer screens may be utilized to enter the information necessary for utilizing the information-based personalized medicine drug discovery system and method of the present invention and to obtain information resulting from utilizing the information-based personalized medicine drug discovery system and method of the present invention.

It will also be understood that the foregoing description is of preferred exemplary embodiments of the invention and that the invention is not limited to the specific forms shown or described herein. Various modifications may be made in the design, arrangement, and type of elements disclosed herein, as well as the steps of utilizing the invention without departing from the scope of the invention as expressed in the appended claims.

The invention claimed is:

1. A method for determining a personalized medical intervention for an individual having a diagnosed pancreatic cancer comprising the steps of:

a) measuring a gene and/or a protein expression level of each of ERBB2, ESR1, PGR, KIT, EGFR, PTGS2 and AR in one or more sample of the individual's pancreatic cancer;

b) comparing the expression levels of the genes and/or proteins measured in step a) to a reference;

c) accessing a computer database to identify at least one drug therapy that interacts with each of the genes and/or proteins that exhibited a change in expression as compared to the reference in step b); and d) providing a computer generated report that identifies the at least one drug therapy identified in step c).

2. The method of claim 1 wherein the identifying step comprises identifying a drug therapy from at least one of an automated review of an extensive literature database and data generated from clinical trials.

3. The method of claim 1 wherein the measuring steps comprise performing at least one of an immunohistochemical (IHC) analysis and a micro array analysis.

4. The method of claim 1 wherein the measuring steps comprises performing an analysis using at least one of an expression micro array, a comparative genomic hybridization (CGH) micro array, a single nucleotide polymorphism (SNP) micro array, a fluorescent in-situ hybridization (FISH), and in-situ hybridization (ISH), and a proteomic array.

5. The method of claim 3 wherein the biological sample comprises a tumor and the immunohistochemical analysis comprises determining whether 30% or more of the tumor cells in the biological sample were +2 or greater staining the target.

6. The method of claim 3 wherein the micro array analysis comprises identifying which genes are up-regulated or down-regulated by determining whether the fold change in expression for a particular gene relative to the reference is significant at $p<0.001$.

7. The method of claim 1 wherein the report includes the individual's test results for the genes and the proteins whose expression was measured and any proposed therapies based on those results.

8. The method of claim 1 wherein the identifying step comprises identifying a plurality of agents that each interact with a different gene or protein wherein the specific agents have not previously been used for treating the individual's diagnosed pancreatic cancer.

9. The method of claim 1 further comprising determining the level of at least one additional protein selected from the group consisting of MLH1, MSH2, CD20, p53, Cyclin D1, bcl2, CD52, PDGFR, AR, CD25, and VEGF.

10. The method of claim 1 further comprising determining the level of at least one additional gene selected from the group consisting of BCL2, HIF1A, PDGFRA, PDGFRB, CDW52, ZAP70, SPARC, GART, GSTP1, NFKBIA, MSH2, TXNRD1, HDAC1, PDGFC, PTEN, CD33, TYMS, RXRB, ADA, TNF, ERCC3, RAF1, VEGF, TOP1, TOP2A, BRCA2, TK1, FOLR2, TOP2B, MLH1, IL2RA, DNMT1, HSPCA, ERBR2, SSTR1, VHL, VDR, POLA, CES2, OGFR, ASNS, NFKB2, RARA, MS4A1, DCK, DNMT3A, EREG, Epiregulin, FOLR1, GNRH1, GNRHR1, FSHB, FSHR, FSHPRH1, folate receptor, HGF, HIG1, IL13RA1, LTB, ODC1, PPARG, PPARGC1, VHL, Lymphotoxin Beta Receptor, Myc, TOP2B, Topoisomerase II, TOPO2B, TXN, VEGFC, ACE2, ADH1C, ADH4, AGT, AREG, CA2, CDK2, caveolin, and NFKB1.

11. The method of claim 1, wherein the biological sample comprises a tumor sample.

12. The method of claim 1, wherein the pancreatic cancer has progressed on standard front line therapy.

13. The method of claim 1, wherein the pancreatic cancer has progressed on at least two chemotherapeutic or hormonal regimens.

14. The method of claim 1, wherein the pancreatic cancer is a metastatic cancer.

15. The method of claim 1, wherein the individual has undergone prior treatment for the diagnosed pancreatic cancer.

16. The method of claim 3, wherein the immunohistochemical (IHC) analysis comprises contacting the biological sample with an antibody to each of the plurality of proteins.

17. The method of claim 3, wherein the micro array analysis comprises contacting the biological sample with primers configured to amplify each of the plurality of genes.

* * * * *